United States Patent
Nishide et al.

(10) Patent No.: US 7,428,290 B2
(45) Date of Patent: Sep. 23, 2008

(54) X-RAY CT APPARATUS

(75) Inventors: Akihiko Nishide, Tokyo (JP); Akira Hagiwara, Tokyo (JP); Yasuhiro Imai, Tokyo (JP); Makoto Gohno, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/534,126

(22) Filed: Sep. 21, 2006

(65) Prior Publication Data

US 2007/0071160 A1    Mar. 29, 2007

(30) Foreign Application Priority Data

Sep. 27, 2005    (JP) .............................. 2005-280512

(51) Int. Cl.
  *H05G 1/60*    (2006.01)
(52) U.S. Cl. .......................................................... 378/4
(58) Field of Classification Search ............... 378/4–20, 378/207, 901
  See application file for complete search history.

(56) References Cited

U.S. PATENT DOCUMENTS

| | | | |
|---|---|---|---|
| 5,241,576 A | | 8/1993 | Lonn |
| 5,377,250 A | * | 12/1994 | Hu .............................. 378/15 |
| 5,473,655 A | * | 12/1995 | Hu ................................ 378/4 |
| 6,173,033 B1 | * | 1/2001 | Klingenbeck-Regn et al. ........................... 378/20 |
| 6,269,141 B1 | * | 7/2001 | Proksa et al. .................. 378/19 |
| 6,470,206 B2 | | 10/2002 | Nukui et al. |
| 6,680,995 B2 | | 1/2004 | Toth et al. |

(Continued)

FOREIGN PATENT DOCUMENTS

EP    0549180 A2    6/1993

(Continued)

OTHER PUBLICATIONS

Akihiko Nishide; Image Processing Apparatus and X-Ray CT Apparatus; U.S. Appl. No. 11/489,969, filed Jun. 20, 2006; 48 pgs.

(Continued)

*Primary Examiner*—Courtney Thomas
*Assistant Examiner*—Alexander H Taningco
(74) *Attorney, Agent, or Firm*—Armstrong Teasdale LLP

(57) ABSTRACT

The present invention is intended to improve image quality ensured by a conventional (axial) scan, a cine scan, or a helical scan performed by an X-ray CT apparatus including a two-dimensional area X-ray detector that has a matrix structure. In helical scan image reconstruction based in three-dimensional image reconstruction performed in an X-ray CT apparatus including a two-dimensional area X-ray detector that is represented by a multi-array X-ray detector or a flat-panel X-ray detector and that has a matrix structure, an image expressing a slice thickness larger than the width of one detector array included in a multi-array X-ray detector is reconstructed according to either of a method of convoluting a z-direction filter to projection data items in the direction of detector arrays (z direction) and a method of convoluting a filer to a tomographic image space in the z direction. The two methods are optimized in terms of a calculation time and tomographic image quality. Consequently, a tomographic image can be quickly reconstructed with high quality.

18 Claims, 21 Drawing Sheets

U.S. PATENT DOCUMENTS

| | | | |
|---|---|---|---|
| 6,862,336 B2 | 3/2005 | Nishide | |
| 6,977,984 B2 * | 12/2005 | Hsieh et al. | 378/4 |
| 2002/0075991 A1 | 6/2002 | Nukui et al. | |
| 2002/0082513 A1 | 6/2002 | Ennen et al. | |
| 2003/0076991 A1 | 4/2003 | Nishide | |
| 2004/0047449 A1 * | 3/2004 | Hagiwara | 378/98.8 |
| 2005/0041772 A1 | 2/2005 | Nishide | |
| 2005/0068029 A1 | 3/2005 | Nishide | |
| 2005/0074085 A1 | 4/2005 | Hsieh et al. | |
| 2005/0201511 A1 * | 9/2005 | Hagiwara et al. | 378/11 |
| 2005/0254617 A1 | 11/2005 | Nishide | |
| 2006/0023831 A1 | 2/2006 | Nishide | |
| 2006/0029285 A1 * | 2/2006 | Hein et al. | 382/260 |
| 2006/0034419 A1 | 2/2006 | Nishide | |
| 2006/0039536 A1 | 2/2006 | Nishide | |
| 2006/0058666 A1 | 3/2006 | Nishide | |
| 2006/0078083 A1 | 4/2006 | Nishide | |
| 2006/0093083 A1 * | 5/2006 | Nishide et al. | 378/17 |
| 2006/0285634 A1 | 12/2006 | Toth | |

FOREIGN PATENT DOCUMENTS

| | | |
|---|---|---|
| EP | 1187070 A2 | 3/2002 |
| JP | 2004-073360 | 3/2004 |
| JP | 2004-230030 | 8/2004 |
| JP | 2004-275440 | 10/2004 |

OTHER PUBLICATIONS

Akihiko Nishide; X-Ray CT Apparatus; U.S. Appl. No. 11/471,198, filed Jun. 20, 2006; 39 pgs.

Akihiko Nishide;X-Ray CT Method and X-Ray CT Apparatus; U.S. Appl. No. 11/471,124, filed Jun. 20, 2006; 40 pgs.

Search Report; Place of Search—'s-Gravenhage; Dated May 25, 2007; NL1032581; 15 pgs.

Samuel Moon-Ho Song et al.; Interpolation of CT Slices for 3-D Visualization by Maximum Intensity Projections; pp. 1065-1075, 2002.

Stefan Schaller; Spiral Interpolation Algorithm for Multislice Spiral CT—Part I: Theory; IEEE Transactions on Medical Imaging, vol. 19, No. 9, Sep. 2000; pp. 822-834.

Theobald Fuchs et al.; Spiral Interpolation Algorithms for Multislice Spiral CT—Part II: Measurement and Evaluation of Slice Sensitivity Profiles and noise at a Clinical Multislice System; IEEE Transactions on Medical Imaging, vol. 19. No. 9, Sep. 2000; pp. 835-847.

Marc Kachelriess et al.; Generalized Multi-Dimensional Adaptive Filtering for Conventional and Spiral Single-Slice, Multi-Slice and Cone-Beam CT; Medical Physics, vol. 28, No. 4, Apr. 2001; pp. 475-490.

Theobald O.J. Fuchs et al.; Fast Volume Scanning Approaches by X-Ray Computed Tomography; Proceedings of the IEEE, vol. 91, No. 10, Oct. 2003; pp. 1492-1502.

H. Bruder et al.; Single-Slice Rebinning Reconstruction in Spiral Cone-Beam Computed Tomography; IEEE Transactions on Medical Imaging, vol. 19, No. 9, Sep. 2000.

* cited by examiner

FIG. 6

|  | z-Direction Filter Convolution to be Applied to Projection Data Items | z-Direction Filter Convolution to be Applied in an Image Space |
|---|---|---|
| Advantage | Once a z-Direction Filter is Convoluted to Projection Data Items and Three-Dimensional Image Reconstruction is Performed once, a Tomographic Image of a Large Slice Thickness is Produced Quickly. | Since a z-Direction Filter is Convoluted in an Image Space in Order to Produce a Tomographic Image of a Large Slice Thickness, z-Direction Filtering can be Achieved Accurately and the Tomographic Image Enjoys High Image Quality. |
| Disadvantage | Since One z-Direction Filter is Convoluted to Projection Data Items in a Direction of Arrays Irrespective of the Position of a Pixel in a Tomographic Image, a Width in an Image Space to which the z-Direction Filter is applied Depends on the Position of a Pixel, and Inconsistency Occurs to cause Artifacts. | Since a Plurality of Tomographic Images are Reconstructed in a z-Direction Direction, a Long Processing Time is Required. |

Projection Data z-Direction Filter Convolution

Image Space z-Direction Filter Convolution

Inconsistency in Width to which Projection Data z-Direction Filter is Applicable.

Image Space z-Direction Filter causing no Inconsistency

Radiographic Flow

Change in Helical Pitch for Variable-Pitch Helical Scan

Slice Sensitivity Profile Concerning Image Space z-Direction Filter Convolution

Influence of Projection Data Space z-Filter Convolution and Image Space z-Filter Convolution on Entire Image Reconstruction Time Flowchart describing Tomography that supports Image Quality Priority Mode and Processing Time Property Mode

FIG. 19

Table Listing Projection Data Space z Filter Coefficients and Image Space z Filter Coefficients in Association with each set of Radiographic Conditions for Helical Scan Region: Lung Field
Object to be Examined: Pneumatosis in Lung Field
Multi-Array X-Ray Detector Mode: Slice
Radiography Mode: Helical Scan
Priority Mode: Image Quality Priority Mode

|  | Artifact Index Value | | | | |
|---|---|---|---|---|---|
| Helical Pitch | 1.0 | 2.0 | 3.0 | 4.0 | 5.0 |
| 0.5 | IZh11/VZh11 | IZh21/VZh21 | IZh31/VZh31 | IZh41/VZh41 | IZh51/VZh51 |
| 0.6 | IZh12/VZh12 | IZh22/VZh22 | IZh32/VZh32 | IZh42/VZh42 | IZh52/VZh52 |
| 0.7 | IZh13/VZh13 | IZh23/VZh23 | IZh33/VZh33 | IZh43/VZh43 | IZh53/VZh53 |
| 0.8 | IZh14/VZh14 | IZh24/VZh24 | IZh34/VZh34 | IZh44/VZh44 | IZh54/VZh54 |
| 0.9 | IZh15/VZh15 | IZh25/VZh25 | IZh35/VZh35 | IZh45/VZh45 | IZh55/VZh55 |
| 1.0 | IZh16/VZh16 | IZh26/VZh26 | IZh36/VZh36 | IZh46/VZh46 | IZh56/VZh56 |
| 1.1 | IZh17/VZh17 | IZh27/VZh27 | IZh37/VZh37 | IZh47/VZh47 | IZh57/VZh57 |
| 1.2 | IZh18/VZh18 | IZh28/VZh28 | IZh38/VZh38 | IZh48/VZh48 | IZh58/VZh58 |
| 1.3 | IZh19/VZh19 | IZh29/VZh29 | IZh39/VZh39 | IZh49/VZh49 | IZh59/VZh59 |
| 1.4 | IZh1A/VZh1A | IZh2A/VZh2A | IZh3A/VZh3A | IZh4A/VZh4A | IZh5A/VZh5A |
| 1.5 | IZh1B/VZh1B | IZh2B/VZh2B | IZh3B/VZh3B | IZh4B/VZh4B | IZh5B/VZh5B |

Note: VZXX Denotes a Coefficient Parameter set of Projection Data Space z Filter Coefficients, and IZxx Denotes a Coefficient Parameter set of Image Space z-Filter Coefficients.

FIG. 20

Table Listing Projection Data Space z Filter Coefficients and Image Space z Filter Coefficients in Association with each set of Radiographic Conditions for Conventional (Axial) Scan Region: Head
Object to be Examined: Cephalic Tumor
Multi-Array X-Ray Detector Mode: Slice
Radiography Mode: Conventional Scan (Axial Scan)
Priority Mode: Image Quality Priority Mode

| Overlap Pitch | Artifact Index Value | | | |
|---|---|---|---|---|
| | 0.5 | 1.0 | 2.0 | 3.0 |
| 0.5 | IZa11/VZa11 | IZa21/VZa21 | IZa31/VZa31 | IZa41/VZa41 |
| 0.6 | IZa12/VZa12 | IZa22/VZa22 | IZa32/VZa32 | IZa42/VZa42 |
| 0.7 | IZa13/VZa13 | IZa23/VZa23 | IZa33/VZa33 | IZa43/VZa43 |
| 0.8 | IZa14/VZa14 | IZa24/VZa24 | IZa34/VZa34 | IZa44/VZa44 |
| 0.9 | IZa15/VZa15 | IZa25/VZa25 | IZa35/VZa35 | IZa45/VZa45 |
| 1.0 | IZa16/VZa16 | IZa26/VZa26 | IZa36/VZa36 | IZa46/VZa46 |

Tomographic Image Produced at End

Tomographic Image Produced at End z Direction

Table Listing Projection Data Space z Filter Coefficients and Image Space z Filter Coefficients in Association with each set of Radiographic Conditions for Helical Scan Region: Abdomen
Object to be Examined: Hepatic Perfusion
Multi-Array X-Ray Detector Mode: Slice
Radiography Mode: Variable-Pitch Helical Scan or Shuttle-Mode Variable Pitch Helical Scan
Priority Mode: Velocity Priority Mode

| Maximum Variable Helical Pitch | Helical Pitch | Noise Index | | | |
|---|---|---|---|---|---|
| | | 8.0 | | 12.0 | |
| | | Artifact Index | | Artifact Index | |
| | | 1.0 | 2.0 | 1.0 | 2.0 |
| 0.5 | 0.0~0.2 | IZs11/VZs11 | IZs21/VZs21 | IZs31/VZs31 | IZs41/VZs41 |
| | 0.2~0.4 | IZs12/VZs12 | IZs22/VZs22 | IZs32/VZs32 | IZs42/VZs42 |
| | 0.4~0.5 | IZs13/VZs13 | IZs23/VZs23 | IZs33/VZs33 | IZs43/VZs43 |
| 1.0 | 0.0~0.3 | IZf11/VZf11 | IZf21/VZf21 | IZf31/VZf31 | IZf41/VZf41 |
| | 0.3~0.7 | IZf12/VZf12 | IZf22/VZf22 | IZf32/VZf32 | IZf42/VZf42 |
| | 0.7~1.0 | IZf13/VZf13 | IZf23/VZf23 | IZf33/VZf33 | IZf43/VZf43 |

Movements made during Shuttle-Mode Variable-Pitch Helical Scan

Movements made during Variable-Pitch Helical Scan

X-RAY CT APPARATUS

CROSS REFERENCE TO RELATED APPLICATIONS

This application claims the benefit of Japanese Application No. 2005-280512 filed Sep. 27, 2005.

BACKGROUND OF THE INVENTION

The present invention relates to an X-ray computed tomography (CT) apparatus for medical use or industrial use, or more particularly, to speed-up in image reconstruction and improvement in image quality for a conventional (axial) scan, a cine scan, or a helical scan.

In X-ray CT apparatuses including a two-dimensional X-ray area detector that is represented by a multi-array X-ray detector or a flat-panel detector and that has a matrix structure, two methods described in FIG. 6 are conceivable as methods for reconstructing an image of a slice thickness that is larger than the width of one detector array included in the multi-array X-ray detector (refer to, for example, Patent Documents 1 and 2). One of the methods is a z-direction filter convolution method (hereinafter, which may be referred to as projection data z-direction filtering) that manipulates projection data, and the other is z-direction filtering that manipulates image space data (hereinafter, which may be referred to as image space z-direction filtering). These methods have the advantage and disadvantage described in FIG. 6.

The above image reconstruction methods for the X-ray CT apparatus have an advantage and a disadvantage, and pose a problem in terms of speed-up in image reconstruction and image quality.

[Patent Document 1] Japanese Unexamined Patent Application Publication No. 2004-73360

[Patent Document 2] Japanese Unexamined Patent Application Publication No. 2004-230030

However, in the above X-ray CT apparatus, as the conical angle of an X-ray cone beam is getting larger, various image reconstruction algorithms are devised. Consequently, the freedom in controlling a slice thickness has increased. On the other hand, an image reconstruction time and image quality relate to each other as trade-offs and are tend to be optimized.

SUMMARY OF THE INVENTION

Therefore, an object of the present invention is to provide an X-ray CT apparatus that includes a two-dimensional area X-ray detector which is represented by a multi-array X-ray detector or a flat-panel X-ray detector and which has a matrix structure, and that optimizes an image reconstruction time and image quality by controlling a slice thickness to be imaged during a conventional (axial) scan, a cine scan, or a helical scan.

The present invention provides an X-ray CT apparatus for medical use or industrial use capable of achieving speed-up in image reconstruction and improvement in image quality when tomographic images expressing various slice thicknesses are reconstructed by performing a conventional (axial) scan, a cine scan, or a helical scan.

According to the first aspect of the present invention, there is provided an X-ray CT apparatus including: an X-ray data acquisition means for acquiring projection data items of X-rays transmitted by a subject, who lies down between an X-ray generator and a two-dimensional X-ray area detector that is opposed to the X-ray generator, that detects X-rays, that is represented by a multi-array X-ray detector or a flat-panel detector, and that has a matrix structure, while rotating the X-ray generator and two-dimensional X-ray area detector about a center of rotation located between the X-ray generator and two-dimensional X-ray area detector; an image reconstruction means for reconstructing an image using projection data items acquired by the X-ray data acquisition means; an image display means for displaying a reconstructed tomographic image; and a radiographic condition designation means for designating radiographic conditions for tomography. The image reconstruction means controls a slice thickness by employing z-direction filter convolution in an image space.

In the X-ray CT apparatus according to the first aspect, tomographic images expressing various slick thicknesses can be reconstructed by performing filter convolution in a z direction perpendicular to a tomographic planes in an image space in consideration of a slice sensitivity profile of sensitivities detected in the z direction perpendicular to the tomographic plane expressed by each tomographic image, and adjusting z-direction filter convolution coefficients while observing the slice sensitivity profile.

According to the second aspect of the present invention, there is provided an X-ray CT apparatus including: an X-ray data acquisition means for acquiring projection data items of X-rays transmitted by a subject, who lies down between an X-ray generator and a two-dimensional X-ray area detector that is opposed to the X-ray generator, that detects X-rays, that is represented by a multi-array X-ray detector or a flat-panel detector, and that has a matrix structure, about a center of rotation located between the X-ray generator and two-dimensional X-ray area detector; an image reconstruction means for reconstructing an image using projection data items acquired by the X-ray data acquisition means; an image display means for displaying a reconstructed tomographic image; and a radiographic condition designation means for designating radiographic conditions for tomography. The image reconstruction means controls a slice thickness by employing z-direction filter convolution in a projection data space.

In the X-ray CT apparatus according to the second aspect, direction-of-arrays (z-direction) filter convolution is performed on projection data items, which are produced by each detector array included in the multi-array X-ray detector, in a projection data space, and z-direction filter convolution coefficients are adjusted. Consequently, tomographic images of various slice thicknesses each expressing a slice sensitivity profile of sensitivities detected in a z direction perpendicular to a tomographic plane can be reconstructed.

According to the third aspect of the present invention, there is provided an X-ray CT apparatus including: an X-ray data acquisition means for acquiring projection data items of X-rays transmitted by a subject, who lies down between an X-ray generator and a two-dimensional X-ray area detector that is opposed to the X-ray generator, that detects X-rays, that is represented by a multi-array X-ray detector or a flat-panel detector, and that has a matrix structure, about a center of rotation located between the X-ray generator and two-dimensional X-ray area detector; an image reconstruction means for reconstructing an image using projection data items acquired by the X-ray data acquisition means; an image display means for displaying a reconstructed tomographic image; and a radiographic condition designation means for designating radiographic conditions for tomography. The image reconstruction means controls a slice thickness by employing z-direction filter convolution in an image space after employing z-direction filter convolution in a projection data space.

In the X-ray CT apparatus according to the third aspect, after direction-of-arrays (z-direction) filter convolution is performed in a projection data space in the same manner as it is according to the second aspect, z-direction filter convolution is performed in an image space in the same manner as it is according to the first aspect. Moreover, direction-of-arrays (z-direction) filter convolution coefficients employed in the projection data space and z-direction filter convolution coefficients employed in the image data space are adjusted. Consequently, tomographic images of various slice thicknesses each expressing a slice sensitivity profile of sensitivities detected in a z direction perpendicular to a tomographic plane can be reconstructed.

According to the fourth aspect of the present invention, there is provided an X-ray CT apparatus identical to the X-ray CT apparatus in accordance with the third aspect except that the image reconstruction means changes at least one of projection data space z-direction filter coefficients and image space z-direction filter coefficient according to each set of radiographic conditions for tomography designated by the radiographic condition designation means.

In the X-ray CT apparatus according to the fourth aspect, the projection data space z-direction filter coefficients and image data space z-direction filter coefficient can be optimized in terms of image quality, a reconstruction time, a radiography time, or radiographic efficiency according to the conditions for tomography designated by the radiographic condition designation means.

According to the fifth aspect of the present invention, there is provided an X-ray CT apparatus identical to the X-ray CT apparatus in accordance with any of the first to fourth aspects except that the image reconstruction means changes at least one of projection data space z-direction filter coefficients and image space z-direction filter coefficients according to an image quality-related radiographic condition for tomography designated by the radiographic condition designation means.

In the X-ray CT apparatus according to the fifth aspect, projection data space z-direction filter coefficients and image data space z-direction filter coefficients are optimized in terms of image quality, a reconstruction time, a radiography time, or radiographic efficiency according to an image quality-related radiographic condition for tomography designated by the radiographic condition designation means.

According to the sixth aspect of the present invention, there is provided an X-ray CT apparatus identical to the X-ray CT apparatus in accordance with any of the first to fifth aspects except that: the radiographic condition designation means designates at least one of an image noise index and an artifact index; and the image reconstruction means changes at least one of image space z-direction filter coefficients and projection data space z-direction filter coefficients according to at least one of the image noise index and artifact index.

In the X-ray CT apparatus according to the sixth aspect, the radiographic condition designation means designates an image noise index in advance. Image space z-direction filter coefficients and projection data space z-direction filter coefficients can be adjusted or optimized so that a target value concerning image noise can be attained.

According to the seventh aspect of the present invention, there is provided an X-ray CT apparatus identical to the X-ray CT apparatus in accordance with any of the first to fifth aspects except that the image reconstruction means changes at least one of projection data space z-direction filter coefficients and image space z-direction filter coefficients according to the radiographic conditions for tomography relevant to a radiography time and radiographic efficiency designated by the radiographic condition designation means.

In the X-ray CT apparatus according to the seventh aspect, projection data space z-direction filter coefficients and image data space z-direction filter coefficients can be optimized in terms of image quality, a reconstruction time, a radiography time, or radiographic efficiency according to the radiographic conditions for tomography concerning the radiography time and radiographic efficiency designated by the radiographic condition designation means.

According to the eighth aspect of the present invention, there is provided an X-ray CT apparatus identical to the X-ray CT apparatus in accordance with any of the first to seventh aspects except that the image reconstruction means performs three-dimensional image reconstruction.

In the X-ray CT apparatus according to the eighth aspect, projection data items produced by the two-dimensional X-ray area detector that is represented by a multi-array X-ray detector or a flat-panel X-ray detector and that has a matrix structure are manipulated in order to reconstruct a three-dimensional image. When a helical scan is performed with a helical pitch set to a small value, image quality does not deteriorate. When a conventional (axial) scan or a cine scan is performed, even if the width of each detector array is larger, the image quality of a tomographic image dependent on each detector array does not deteriorate. Thus, a tomographic image of improved quality can be reconstructed.

According to the ninth aspect of the present invention, there is provided an X-ray CT apparatus identical to the X-ray CT apparatus in accordance with any of the first to eighth aspects except that the image reconstruction means changes image space z-direction filter coefficients and projection data space z-direction filter coefficients according to a slice thickness of a tomographic image.

In the X-ray CT apparatus according to the ninth aspect, projection data space direction-of-arrays (z-direction) filter convolution coefficients and image data space z-direction filter convolution coefficients are adjusted in order to produce tomographic images of various slice thicknesses expressing various slice sensitivity profiles. Consequently, tomographic images of various slice thicknesses expressing slice sensitivity profiles of sensitivities detected in a z direction perpendicular to a tomographic plane.

According to the tenth aspect of the present invention, there is provided an X-ray CT apparatus identical to the X-ray CT apparatus in accordance with any of the first to ninth aspects except that the image reconstruction means changes image space z-direction filter coefficients and projection data space z-direction filter coefficients according to the width of each array included in the X-ray detector in the direction of arrays and the number of detector arrays.

In the X-ray CT apparatus according to the tenth aspect, projection data space direction-of-arrays (z-direction) filter coefficients and image data space z-direction filter convolution coefficients are adjusted according to the thickness of each detector array in the direction of arrays (z direction) and the number of detector arrays. Herein, the filter coefficients are applied to X-ray detector data items or projection data items read from a two-dimensional X-ray area detector that is represented by a multi-array X-ray detector or a flat-panel X-ray detector and that has a matrix structure. Consequently, tomographic images of various slice thicknesses expressing various slice sensitivity profiles of sensitivities detected in a z direction perpendicular to a tomographic plane can be reconstructed.

According to the eleventh aspect of the present invention, there is provided an X-ray CT apparatus identical to the X-ray CT apparatus in accordance with any of the first to tenth aspects except that the image reconstruction means changes image space z-direction filter coefficients and projection data space z-direction filter coefficients according to the position of each pixel in a tomographic image of an xy plane reconstructed.

In the X-ray CT apparatus according to the eleventh aspect, projection data space direction-of-arrays (z-direction) filter coefficients and image data space z-direction filter coefficients are adjusted in consideration of a slice sensitivity profile to be expressed in a z direction by the pixels constituting a reconstructed tomographic image of an xy plane. Consequently, tomographic images of various slice thicknesses expressing various slice sensitivity profiles of sensitivities detected in the z direction perpendicular to a tomographic plane can be produced.

According to the twelfth aspect of the present invention, there is provided an X-ray CT apparatus identical to the X-ray CT apparatus in accordance with any of the first to eleventh aspects except that the image reconstruction means sets the image space z-direction filter coefficients to positive values.

In the X-ray CT apparatus according to the twelfth aspect, when the image space z-direction filter coefficients are all positive values, a tomographic image is produced to express a slice thickness equivalent to a length in a z direction in which the positive coefficients are applied. Moreover, a tomographic image is produced to express a slice sensitivity profile according to the convolution of the positive coefficients.

According to the thirteenth aspect of the present invention, there is provided an X-ray CT apparatus identical to the X-ray CT apparatus in accordance with any of the first to eleventh aspects except that the image reconstruction means sets part of the image space z-direction filter coefficients to negative values.

In the X-ray CT apparatus according to the thirteenth aspect, when part of the image space z-direction filter coefficients are negative values, a tomographic image is produced as a difference image between a tomographic image resulting from employment of positive coefficients and a tomographic image resulting from employment of negative coefficients. Moreover, a tomographic image is produced to express a slice sensitivity profile according to the convolution of the coefficients.

According to the fourteenth aspect of the present invention, there is provided an X-ray CT apparatus identical to the X-ray CT apparatus in accordance with any of the first to thirteenth aspects except that the image reconstruction means sets the projection data space z-direction filter coefficients to positive values.

In the X-ray CT apparatus according to the fourteenth aspect, when the projection data space direction-of-arrays (z-direction) filter coefficients are all positive values, a tomographic image is produced to express a slice thickness equivalent to a length in a direction of arrays (z direction) in which the positive coefficients are applied. Moreover, a slice sensitivity profile is expressed according to the convolution of the positive coefficients.

According to the fifteenth aspect of the present invention, there is provided an X-ray CT apparatus identical to the X-ray CT apparatus in accordance with any of the first to thirteenth aspects except that the image reconstruction means sets part of the projection data space z-direction filter coefficients to negative values.

In the X-ray CT apparatus according to the fifteenth aspect, when part of the projection data space direction-of-arrays (z-direction) filter coefficients are negative values, a tomographic image is produced as a difference image between a tomographic image resulting from employment of the positive coefficients and a tomographic image resulting from employment of the negative coefficients. Moreover, a slice sensitivity profile is expressed according to the coefficients.

According to the sixteenth aspect of the present invention, there is provided an X-ray CT apparatus identical to the X-ray CT apparatus in accordance with any of the first to fifteenth aspects except that the image reconstruction means concurrently performs at least two of z-direction filter convolution in a projection data space, back projection, and z-direction filter convolution in an image space.

In the X-ray CT apparatus according to the sixteenth aspect, filter coefficients employed in image space z-direction filter convolution that requires a long image reconstruction time, and filter coefficients employed in projection data space z-direction filer convolution that requires a short image reconstruction time are adjusted or optimized. Consequently, tomographic images of various slice thicknesses are reconstructed to express various slice sensitivity profiles of sensitivities detected in a z direction perpendicular to a tomographic plane.

According to the seventeenth aspect of the present invention, there is provided an X-ray CT apparatus identical to the X-ray CT apparatus in accordance with any of the first to sixteenth aspects except that the image reconstruction means controls a slice thickness by employing projection data space z-direction filter convolution and image space z-direction filter convolution, and reconstructs a tomographic image by performing a helical scan.

In the X-ray CT apparatus according to the seventeenth aspect, when a helical scan is performed, filter coefficients employed in image space z-direction filter convolution that ensures high image quality but requires a long image reconstruction time, and filter coefficients employed in projection data space z-direction filter convolution in which a small helical pitch leads to deteriorated image quality and a short image reconstruction time is required are adjusted or optimized. Consequently, tomographic images of various slice thicknesses are produced to express various slice sensitivity profiles of sensitivities detected in a z direction perpendicular to a tomographic plane.

According to the eighteenth aspect of the present invention, there is provided an X-ray CT apparatus identical to the X-ray CT apparatus in accordance with any of the first to sixteenth aspects except that the image reconstruction means controls a slice thickness by employing projection data space z-direction filter convolution and image space z-direction filter convolution, and reconstructs a tomographic image by performing a variable-pitch helical scan.

In the X-ray CT apparatus according to the eighteenth aspect, when a variable-pitch helical scan is performed, filter coefficients employed in image space z-direction filter convolution that ensures high image quality but requires a long image reconstruction time, and filter coefficients employed in projection data space z-direction filter convolution in which a small helical pitch leads to deteriorated image quality and a short image reconstruction time is required are adjusted or optimized. Consequently, tomographic images of various slice thicknesses are reconstructed to express various slice sensitivity profiles of sensitivities detected in a z direction perpendicular to a tomographic plane.

According to the nineteenth aspect of the present invention, there is provided an X-ray CT apparatus identical to the X-ray CT apparatus in accordance with the seventeenth to eighteenth aspect except that the image reconstruction means changes image space z-direction filter coefficients and projection data space z-direction filter coefficients dependently on a helical pitch set for a helical scan or a variable-pitch helical scan.

In the X-ray CT apparatus according to the nineteenth aspect, an initial slice thickness is determined by performing projection data space z-direction filter convolution that employs projection data space z-direction filter coefficients dependent on a helical pitch set for a helical scan or a variable-pitch helical scan. Moreover, a final slice thickness is determined by performing image space z-direction filter convolution that employs image space z-direction filter coefficients.

In particular, when acceleration or deceleration is made during a variable-pitch helical scan, an initial slice thickness is determined by performing projection data space z-direction filter convolution that employs projection data space z-direction filter coefficients dependent on a range of helical pitches that change with the passage of time. Moreover, a final slice thickness is determined by performing image space z-direction filter convolution that employs image space z-direction filter coefficients.

According to the twentieth aspect of the present invention, there is provided an X-ray CT apparatus identical to the X-ray CT apparatus in accordance with any of the first to sixteenth aspects except that the image reconstruction means controls a slice thickness by performing projection data space z-direction filter convolution and image space z-direction filter convolution, and reconstructs a tomographic image by performing a conventional (axial) scan or a cine scan.

In the X-ray CT apparatus according to the twentieth aspect, when a conventional (axial) scan or a cine scan is performed, filter coefficients employed in image space z-direction filter convolution that ensures high image quality but requires a long image reconstruction time, and filter coefficients employed in projection data space z-direction filter convolution in which a small helical pitch leads to deteriorated image quality and a short image reconstruction time is required are adjusted or optimized. Consequently, tomographic images of various slice thicknesses are reconstructed to express various slice sensitivity profiles of sensitivities detected in a z direction perpendicular to a tomographic plane.

According to an X-ray CT apparatus or an X-ray CT image reconstruction method in which the present invention is implemented, when a conventional (axial) scan, a cine scan, or a helical scan is performed using an X-ray CT apparatus including a two-dimensional area X-ray detector that is represented by a multi-array X-ray detector or a flat-panel X-ray detector and that has a matrix structure, a slice thickness can be controlled and an image reconstruction time and image quality can be optimized.

Further objects and advantages of the present invention will be apparent from the following description of the preferred embodiments of the invention as illustrated in the accompanying drawings.

BRIEF DESCRIPTION OF THE DRAWINGS

FIG. 6 is a table listing the advantage and disadvantage of a method of convoluting a z-direction filter to projection data items in comparison with those of a method of convoluting a z-direction filter to an image space.

FIG. 19 shows a table listing projection data space z filter coefficients and image space z filter coefficients in association with each set of radiographic conditions.

FIG. 20 shows a table listing projection data space z filter coefficients and image space z filter coefficients in association with each set of radiographic conditions for a conventional (axial) scan.

FIG. 22 shows a table listing projection data space z filter coefficients and image space z filter coefficients in association with each set of radiographic conditions for a variable-pitch helical scan.

DETAILED DESCRIPTION OF THE INVENTION

The present invention will be described below by taking an illustrated embodiment for instance. Noted is that the present invention will not be limited to the embodiment.

Figure 1:
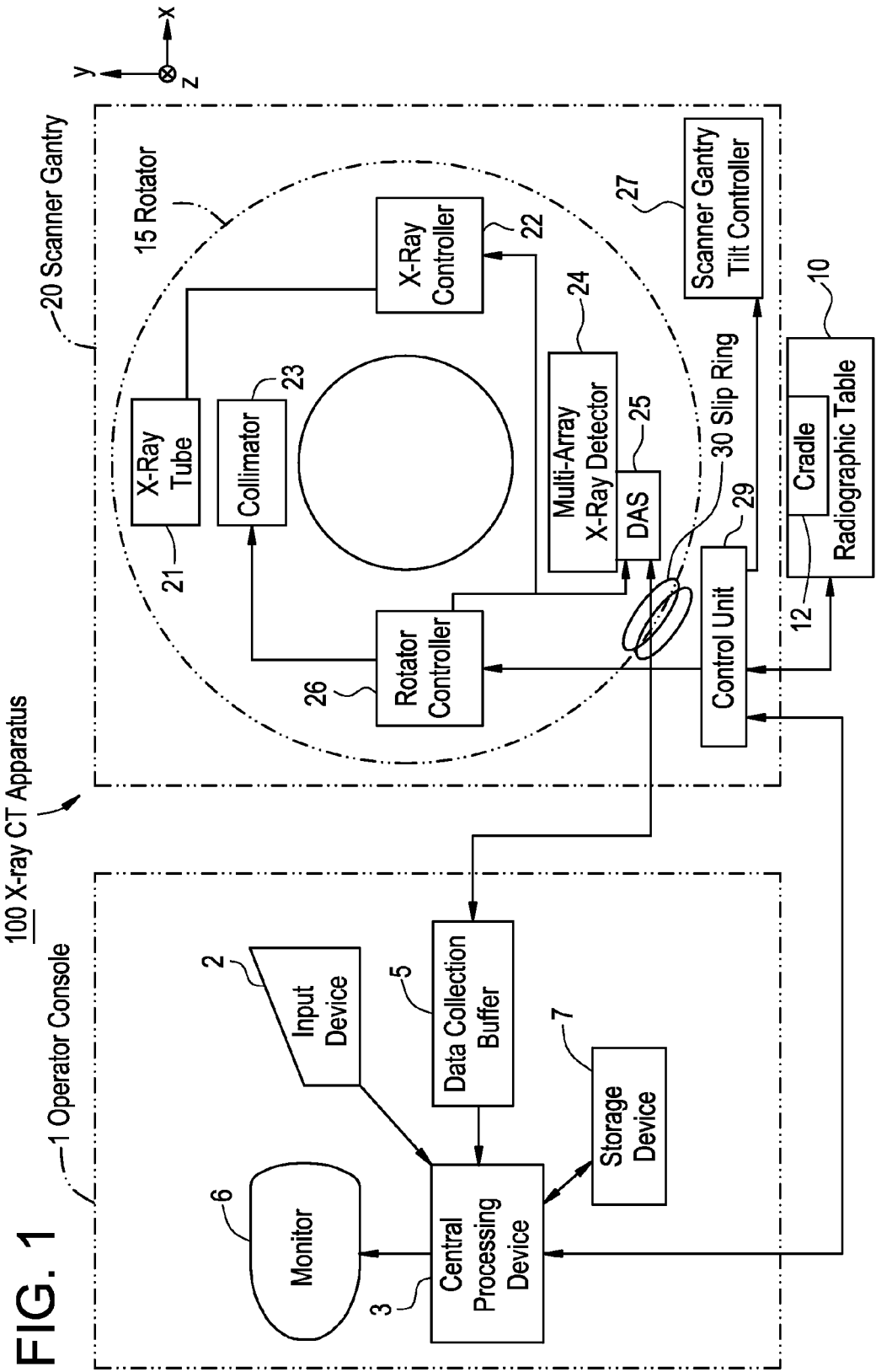
FIG. 1 is a block diagram showing an X-ray CT apparatus in accordance with an embodiment of the present invention.

FIG. 1 is a block diagram showing the configuration of an X-ray CT apparatus in accordance with an embodiment of the present invention. The X-ray CT apparatus 100 includes an operator console 1, a radiographic table 10, and a scanner gantry 20.

The operator console 1 includes: an input device 2 that receives an operator's entry, a central processing device 3 that executes preprocessing, image reconstruction, post-processing, and others; a data collection buffer 5 in which X-ray detector data items acquired by the scanner gantry 20 are collected; a monitor 6 on which a tomographic image reconstructed using projection data items produced by preprocessing the X-ray detector data items is displayed; and a storage device 7 in which programs, X-ray detector data items, projection data items, and X-ray tomographic images are stored.

The radiographic table 10 includes a cradle 12 which carries a subject, who lies down on the cradle, into or out of a bore of the scanner gantry 20. The cradle 12 is lifted, lowered, and rectilinearly moved by a motor incorporated in the radiographic table 10.

The scanner gantry 20 includes: an X-ray tube 21, an X-ray controller 22, a collimator 23, a multi-array X-ray detector 24, a data acquisition system (DAS) 25, a rotator controller 26 that controls the X-ray tube 21 and others which rotate about a subject's body axis, and a control unit 29 that transfers control signals and others to or from the operator control 1 and radiographic table 10. Moreover, a scanner gantry tilt controller 27 allows the scanner gantry 20 to tilt forwards or backwards in a z direction by approximately ±30°.

Figure 2:
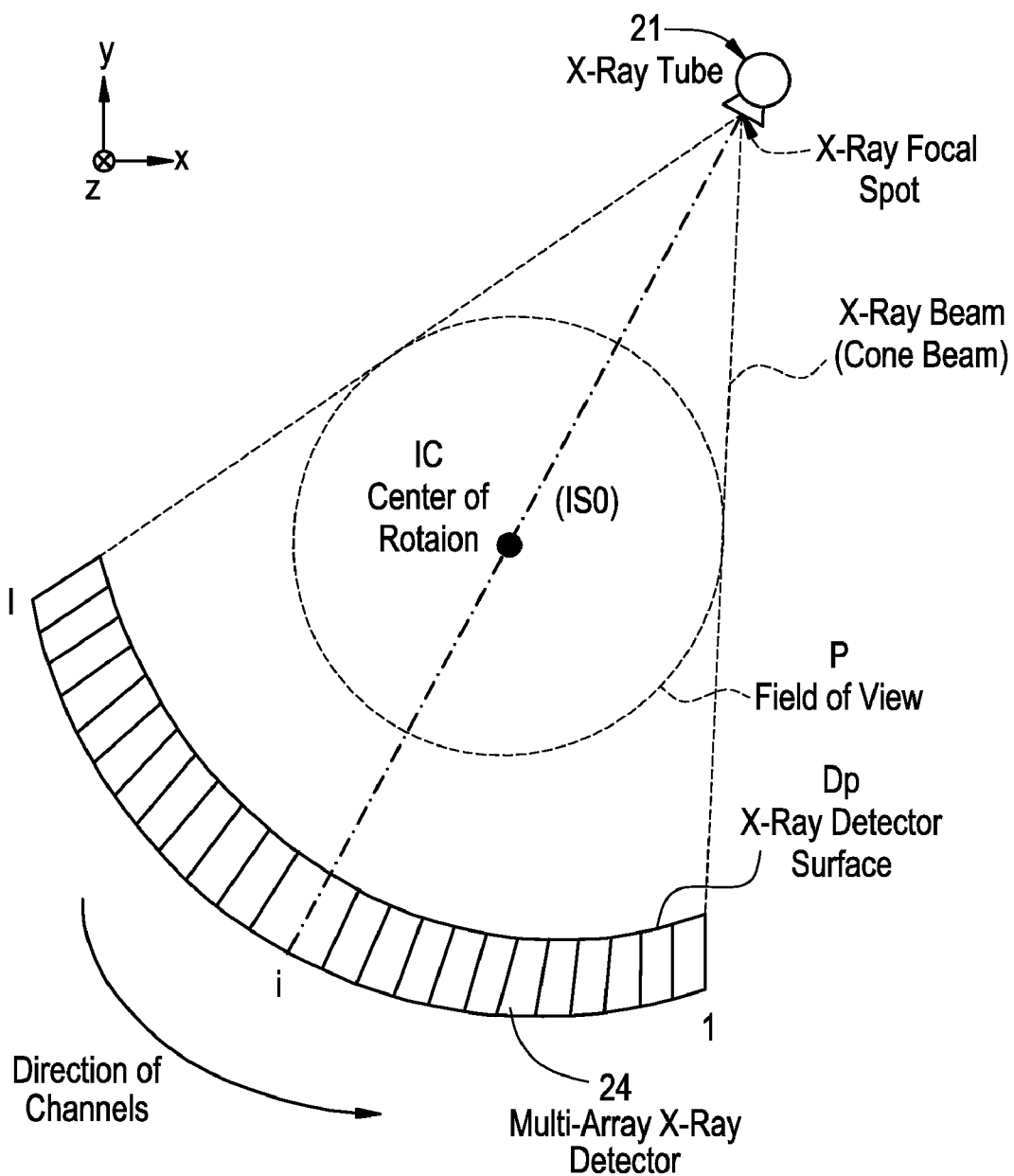
FIG. 2 is an explanatory diagram showing rotation of an X-ray generator (X-ray tube) and a multi-array X-ray detector.

FIG. 2 is an explanatory diagram showing the geometric arrangement of the X-ray tube 21 and multi-array X-ray detector 24.

The X-ray tube and multi-array X-ray detector 24 rotate about a center of rotation IC. Assuming that a vertical direction is regarded as a y direction, a horizontal direction is regarded as an x direction, and a table advancing direction perpendicular to the x and y directions is regarded as a z direction, a rotational plane on which the X-ray tube 21 and multi-array X-ray detector 24 rotate is an xy plane. Moreover, a moving direction in which the cradle 12 moves is the z direction.

The X-ray tube 21 generates an X-ray beam called a cone beam CB. When the center-axis direction of the cone beam CB is parallel to the y direction, the X-ray tube shall be located at a view angle 0°.

The multi-array X-ray detector 24 includes, for example, 256 X-ray detector arrays. Each X-ray detector array includes, for example, 1024 X-ray detector channels.

X-rays are irradiated, and projection data items are produced by the multi-array X-ray detector 24 and acquired by the DAS 25. The projection data items are then analog-to-digital converted, and transferred to the data collection buffer 5 via a slip ring 30. The data items transferred to the data collection buffer 5 are manipulated by the central processing device 3 according to a program read from the storage device 7. A tomographic image is then reconstructed and displayed on the monitor 6.

Figure 3:
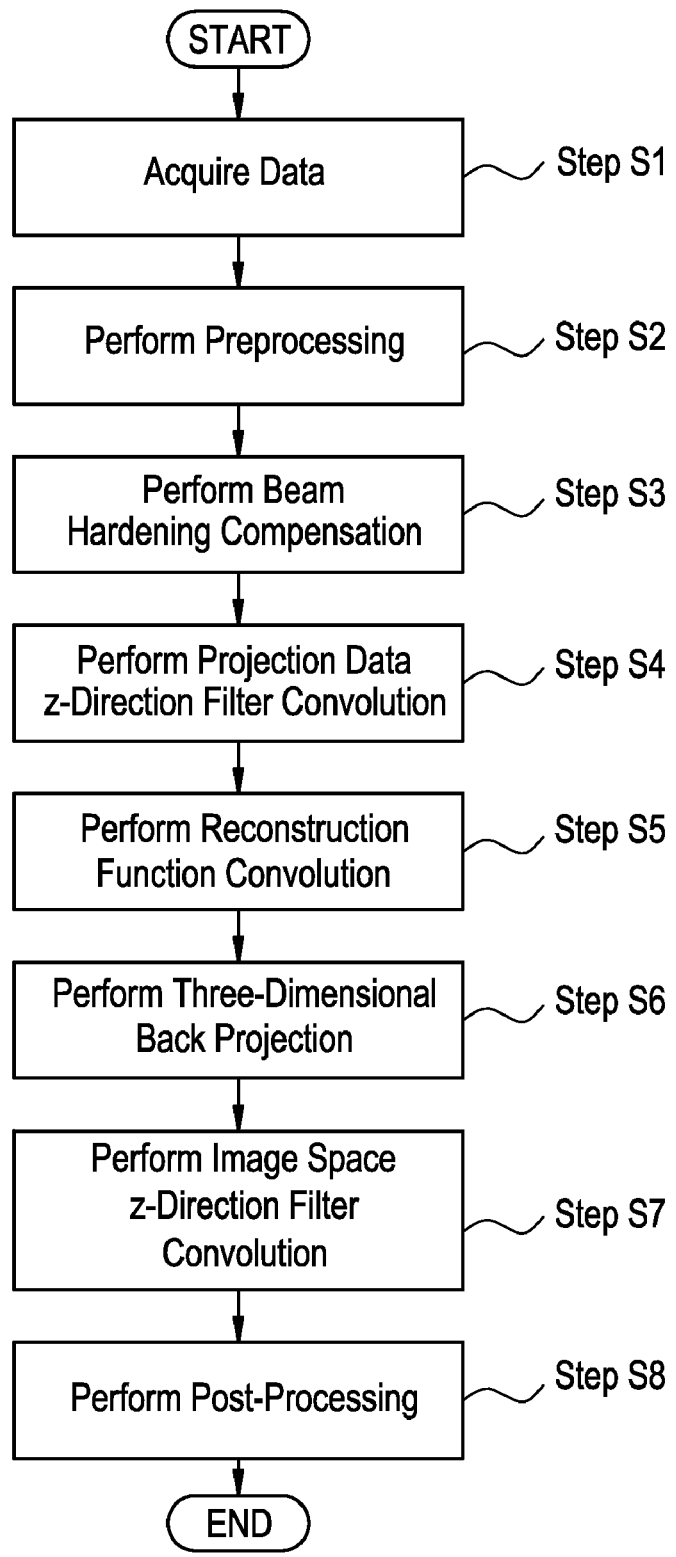
FIG. 3 is a flowchart outlining actions to be performed in the X-ray CT apparatus in accordance with the embodiment of the present invention.

FIG. 3 is a flowchart outlining actions to be performed in the X-ray CT apparatus 100 in accordance with the present invention.

At step S1, when a helical scan is performed, the X-ray tube 21 and multi-array X-ray detector 24 are rotated about a subject, and the cradle 12 on the radiographic table 10 is rectilinearly moved. Meanwhile, X-ray detector data items are acquired. Herein, each X-ray detector data D0(view,j,i) is identified with a view angle view, a detector array number j, and a channel number i. Data of a table position in a z direction of rectilinear movement, Ztable(view), is appended to each of the X-ray detector data items. In contrast, when a conventional (axial) scan or a cine scan is performed, the cradle 12 on the radiographic table 10 is immobilized at a certain z-direction position, but the data acquisition system is rotated by one turn or a plurality of turns in order to acquire X-ray detector data items. If necessary, after the cradle is moved to the next z-direction position, the data acquisition system is rotated by one turn or a plurality of turns in order to acquire X-ray detector data items. Herein, the view angle view is an angle by which the X-ray tube 21 is rotated from a position, which is located above a subject in a vertical direction (y-axis direction), about the subject. Moreover, the detector array number j is a number indicating the position of X-ray detector elements juxtaposed in a direction of arrays (z-axis direction) in the multi-array X-ray detector 24. Moreover, the channel number i is a number indicating the position of X-ray detector elements juxtaposed in a direction of channels in the multi-array X-ray detector 24. Moreover, the X-ray detector data D0(view,j,i) is data which an X-ray detector element that is located at a position identified with the detector array number j and channel number i within the multi-array X-ray detector 24 acquires by detecting X-rays transmitted by the subject. Moreover, the table position in the z direction of rectilinear movement, Ztable(view), is a position to which the cradle 12 on the radiographic table 10 is moved in the direction of the subject's body axis (z-axis direction) during a scan.

At step S2, the X-ray detector data items D0(view,j,i) are preprocessed and converted into projection data items. The preprocessing includes, as described in FIG. 4, offset nulling of step S21, logarithmic conversion of step S22, X-ray dose correction of step S23, and sensitivity correction of step S24.

At step S3, beam hardening compensation is performed on the preprocessed projection data items D1(view,j,i). Assuming that D1(view,j,i) denotes the projection data items having undergone the sensitivity correction S24 included in the preprocessing S2 and D11(view,j,i) denotes data items having undergone the beam hardening compensation S3, the beam hardening compensation S3 is expressed by the formula (1) presented below, for example, a polynomial expression.

$$D11(view,j,i) = D1(view,j,i) \cdot (B_0(j,i) + B_1(j,i) \cdot D1(view,j,i) + B_2(j,i) \cdot D1(view,j,i)^2) \quad (1)$$

At step S4, projection data z-direction filtering is performed on the projection data items D11(view,j,i), which have undergone the beam hardening compensation, in order to filter the projection data items in the z direction (direction of arrays).

At step S4, a direction-of-arrays filter whose size is equivalent to five arrays as presented as the formula (2) below is applied to projection data items D11(ch, row) (where ch ranges 1 to CH and row ranges from 1 to ROW) that have been undergone the beam hardening compensation after preprocessed by a data acquisition system including each detector array of the multi-array X-ray detector determined with each view angle.

$$(w1(ch), w2(ch), w3(ch), w4(ch), w5(ch)) \quad (2)$$

Herein, the condition expressed by the formula (3) presented below shall be satisfied.

$$\sum_{k=1}^{5} w_k(ch) = 1 \quad (3)$$

The corrected detector data items D12(ch,row) are expressed by the formula (4).

$$D12(ch, j) = \sum_{k=1}^{5} (D11(ch, i-k-3) \cdot w_k(ch)) \quad (4)$$

A slice thickness can be controlled based on a distance from a center of a field of view by changing the coefficients of the direction-of-arrays filter. In general, the slice thickness in the center of a field of view expressed by a tomographic image is larger than the one in the perimeter thereof. The direction-of-arrays filter coefficients are optimally changed between the center of a field of view and the perimeter thereof so that the slice thickness will be nearly uniform over the center and perimeter of the field of view expressed by a tomographic image.

At step S5, reconstruction function convolution is performed. Specifically, data items are Fourier-transformed, applied a reconstruction function, and then inverse-Fourier-transformed. Assuming that D12 denotes data items having undergone the z-direction filter convolution, D13 denotes data items having undergone the reconstruction function convolution, and Kernel (j) denotes the reconstruction function to be convoluted, the reconstruction function convolution S5 is expressed by the formula (5) below.

$$D13(\text{view},j,i)=D12(\text{view},j,i)*\text{Kernel}(j) \tag{5}$$

At step S6, three-dimensional back projection is performed on projection data items D13 (view,j,i) having undergone the reconstruction function convolution in order to produce back projection data items D3 (x,y,z). An image to be reconstructed is a three-dimensional image expressing a plane perpendicular to the z axis or parallel to the xy plane. The three-dimensional back projection will be described later with reference to FIG. 5.

At step S7, image space z-direction filter convolution is performed on the back-projected tomographic image D3(x,y,z). Assuming that D4(x,y,z) denotes a tomographic image having undergone the image space z-direction filter convolution, the image space z-direction filter convolution is expressed by the formula (6).

$$D4(x, y, z) = \sum_{i=-1}^{1} D3(x, y, z+i) \cdot v(i) \tag{6}$$

Herein, v(i) denotes image space z-direction filter coefficients that are applied to a z-direction width equivalent to 2l+1 values and that are expressed as a sequence provided by the formula (7) below.

$$v(-1),v(-1+1),\ldots v(-1),v(0),v(1),\ldots v(1-1),v(1) \tag{7}$$

In helical scanning, the image space filter coefficients v(i) may be independent of a z-direction position. Assuming that the two-dimensional X-ray area detector 24 that is wide in the z direction is adopted as the multi-array X-ray detector 24, when a conventional (axial) scan or a cine scan is performed, the image space z-direction filter coefficients v(i) should depend on a z-direction position of an X-ray detector array so that each tomographic image can be finely adjusted dependently on the position of an array.

At step S8, post-processing including image filter convolution and CT number transformation is performed on a tomographic image D4 (x,y,z) having undergone the image space z-direction filter convolution in order to produce a tomographic image D41(x,y,z).

In the image filter convolution included in the post-processing, assuming that D41(x,y,z) denotes a tomographic image having undergone three-dimensional back projection, D42(x,y,z) denotes data items having undergone image filter convolution, and Filter(z) denotes an image filter that is a two-dimensional filter to be applied to the xy plane regarded as a tomographic plane, the image filter convolution is expressed by the formula (8) below.

$$D42(x,y,z)=D41(x,y,z)*\text{Filter}(z) \tag{8}$$

Since image filter convolution can be independently performed on data items produced by each detector array j, a difference in the characteristics of one detector array concerning noises and a resolution from the characteristics of another detector array can be compensated.

A produced tomographic image is displayed on the monitor 6.

Figure 4:
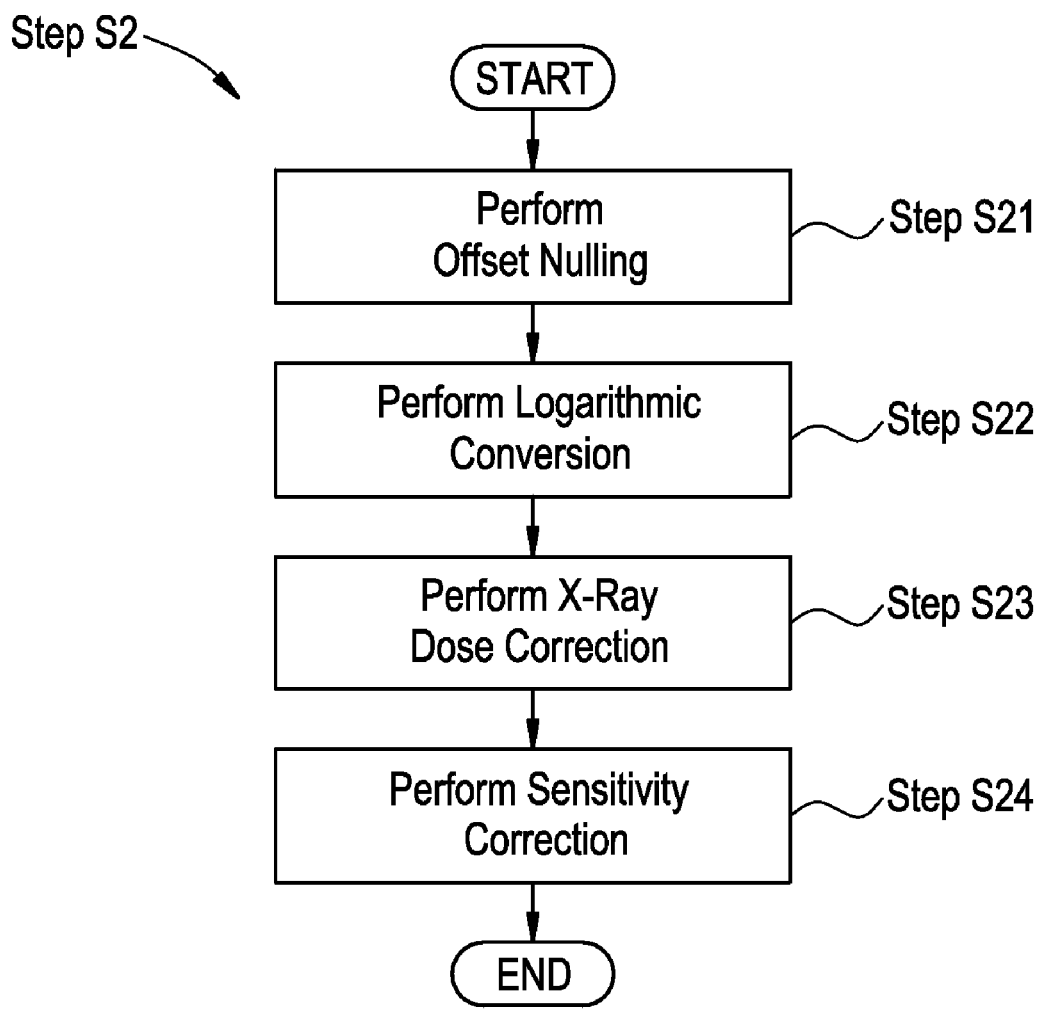
FIG. 4 is a flowchart describing preprocessing.
Figure 5:
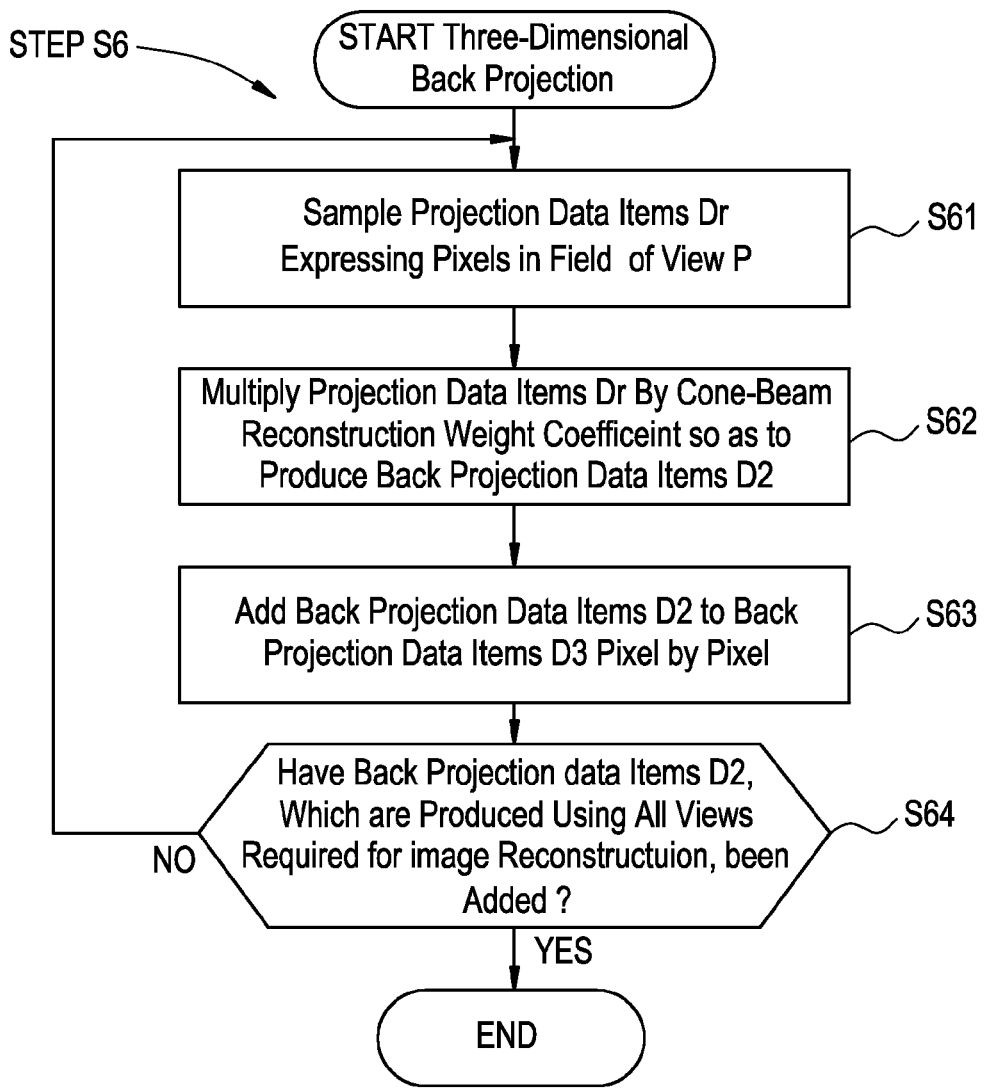
FIG. 5 is a flowchart describing three-dimensional image reconstruction.

FIG. 5 is a flowchart describing three-dimensional back projection (step S6 in FIG. 4).

According to the present invention, an image to be reconstructed is a three-dimensional image expressing a plane perpendicular to the z axis or parallel to the xy plane. Hereinafter, a field of view P shall be parallel to the xy plane.

At step S61, one of all views required for reconstruction of a tomographic image (that is, views produced by rotating the scanner gantry 360° or "180°+the angle of a fan beam") is focused, and projection data items Dr expressing pixels in the field of view P are sampled.

A square field having 512 pixels arrayed in rows and in columns and being parallel to the xy plane shall be the field of view P. Lines T0 to T511 shall be produced by projecting lines of pixels, which start with a line of pixels L0 parallel to the x axis and extending from a point y=0 and end with a line of pixels L511 extending from a point y=511, onto the surface of the multi-array X-ray detector 24 in the direction of X-ray transmission. Projection data items are sampled from the lines T0 to T511. The projection data items are regarded as projection data items Dr(view,x,y) to be back-projected to the respective pixels in a tomographic image. Herein, x and y correspond to x- and y-coordinates indicating the position (x,y) of each pixel in a tomographic image.

The direction of X-ray transmission is determined by the geometrical positions of the X-ray focal spot in the X-ray tube 21 and the multi-array X-ray detector 24. Since the z-coordinate z(view) contained in each X-ray detector data D0(view,j,i) is known to correspond to a table position in a z direction of rectilinear movement Ztable(view), even if X-ray detector data D0(view,j,i) is acquired during acceleration or deceleration, the direction of X-ray transmission can be accurately detected based on a geometric data acquisition system including the X-ray focal spot and a detector array of the multi-array X-ray detector.

For example, part of a line may come out of the multi-array X-ray detector 24 in the direction of channels in the same manner as, for example, part of the line T0 produced by projecting the line of pixels L0 on the surface of the multi-array X-ray detector 24 in the direction of X-ray transmission does. In this case, projection data items Dr(view,x,y) to be detected from the line are set to 0s. If part of a line comes out in the z direction, missing projection data items Dr(view,x,y) are extrapolated.

As mentioned above, projection data items Dr(view,x,y) expressing the pixels in the field of view P are sampled.

Referring back to FIG. 5, at step S62, the projection data items Dr(view,x,y) are multiplied by a cone-beam reconstruction weight coefficient in order to produce projection data items D2(view, x,y).

Herein, the cone-beam reconstruction weight coefficient w(i,j) will be described below. In the case of fan-beam image reconstruction, generally, assuming that a straight line linking the focal spot in the X-ray tube 21 set at a view angle view=βa and a pixel g(x,y) in the field of view P (xy plane) meets a center axis Bc of an X-ray beam at an angle γ, and an opposite view angle is view=βb, the opposite view angle βb is expressed by the formula (9) below.

$$\beta b=\beta a+180°-2\gamma \tag{9}$$

Assuming that αa and αb denote angles at which an X-ray beam passing through a pixel g(x,y) in the field of view P and the opposite X-ray beam meet the field of view P, projection data items are, as expressed by the formula (10) below, multiplied by the cone-beam reconstruction weight coefficient ωa or ωb dependent on the angle αa or αb in order to produce back projection data items D2(0,x,y).

$$D2(0,x,y)=\omega a \cdot D2(0,x,y)\_a + \omega b \cdot D2(0,x,y)\_b \qquad (10)$$

Herein, D2(0,x,y)_a denotes projection data items at the view angle βa, and D2(0,x,y)_b denotes projection data items at the view angle βb.

Incidentally, the sum of the cone-beam reconstruction weight coefficients ωa and ωb associated with the X-ray beam and opposite X-ray beam is a unity as expressed by the formula (11) below.

$$\omega a + \omega b = 1 \qquad (11)$$

Projection data items are multiplied by either of the cone-beam reconstruction weight coefficients ωa and ωb, and the resultant sets of projection data items are summated. This is helpful in reducing conical angle artifacts.

Moreover, in the case of fan-beam image reconstruction, the projection data items expressing the pixels in the field of view P are multiplied by a distance coefficient. The distance coefficient is provided as $(r1/r0)^2$ where r0 denotes a distance from the focal spot in the X-ray tube 21 to a detector element that belongs to a detector array j and a channel i included in the multi-array X-ray detector 24 and that detects projection data Dr, and r1 denotes a distance from the focal spot in the X-ray tube 21 to a pixel in the field of view P represented by the projection data Dr.

In the case of parallel-ray beam image reconstruction, the projection data items expressing the pixels in the field of view P are multiplied by the cone-beam reconstruction weight coefficient w(i,j) alone.

At step S63, the projection data items D2(view,x,y) are added pixel by pixel to the back projection data items D3(x,y) that are cleared in advance.

Figure 10:
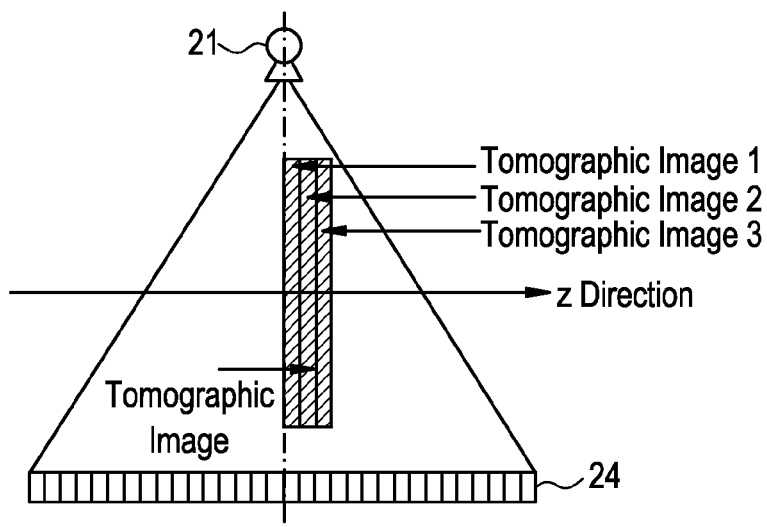
FIG. 10 shows an image space z-direction filter that causes no inconsistency.

At step S64, steps S61 to S63 are repeated for all views required for reconstruction of a tomographic image (that is, views produced by rotating the scanner gantry 360° or "180°+ the angel of a fan beam") in order to produce a back-projected tomographic image D3(x,y) shown in FIG. 10. The tomographic image is regarded as a tomographic image D3(x,y,z) representing a plane located at a position indicated with a certain z-coordinate.

Incidentally, the field of view P may not be a square field having 512 pixels arrayed in rows and in columns but may be a round field having a diameter of 512 pixels long.

Figure 7:
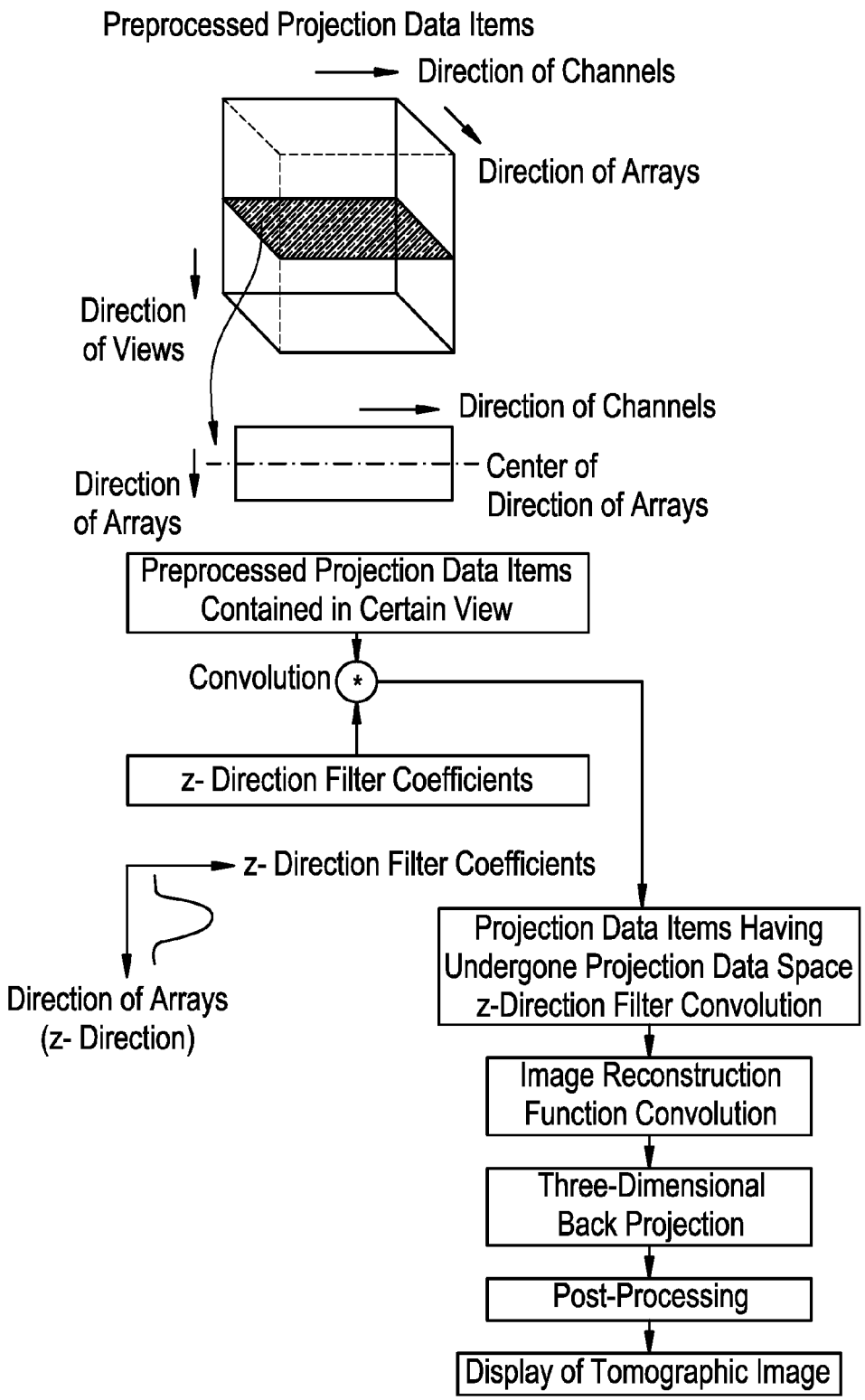
FIG. 7 shows projection data z-direction filter convolution.
Figure 8:
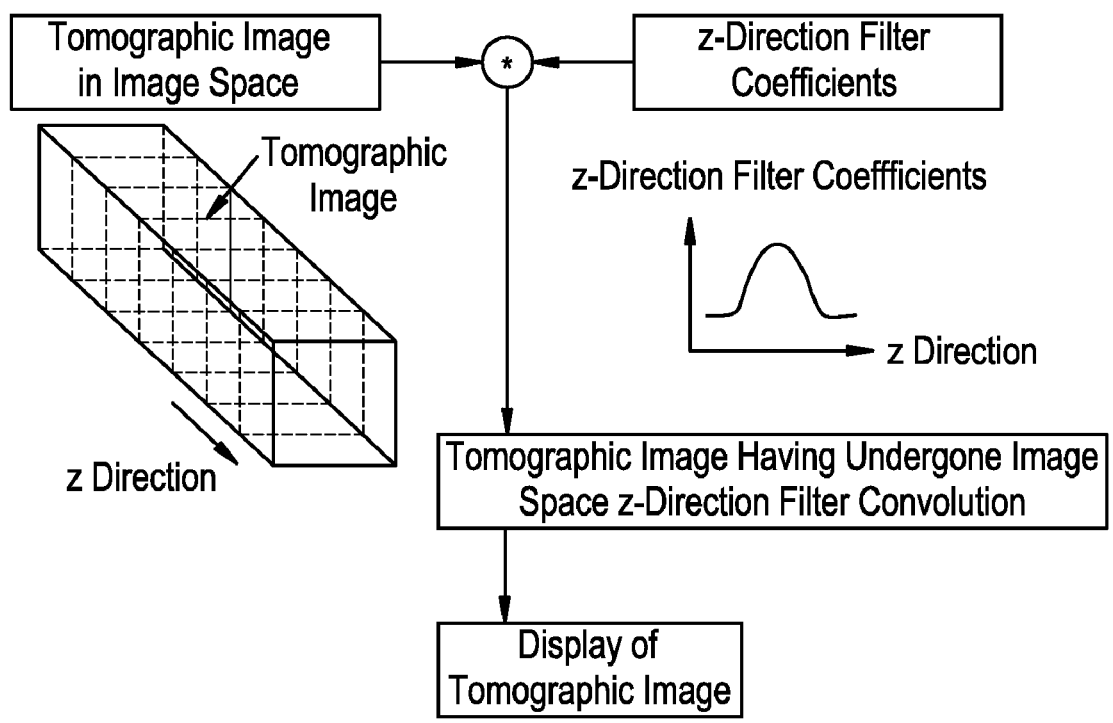
FIG. 8 shows image space z-direction filter convolution.

In general, as listed in the table of FIG. 6, a technology for controlling a slice thickness in an X-ray CT apparatus includes a z-direction filter convolution method to be applied to projection data items as shown in FIG. 7 and a z-direction filter convolution method to be applied to image space data items as shown in FIG. 8.

As listed in the table of FIG. 6, the z-direction filter convolution method to be applied to projection data items has the advantage that a tomographic image expressing a large slice thickness can be quickly produced merely by convoluting a z-direction filter to projection data items and performing three-dimensional image reconstruction once. The disadvantage of the z-direction filter convolution method to be applied to projection data items is that one kind of z-direction filter is convoluted to projection data items in the direction of arrays irrespective of the positions of pixels in a tomographic image. Therefore, a width in an image space to which the z-direction filter is applied depends on the positions of pixels. Consequently, the width of an X-ray beam to be back projected becomes inconsistent with the width in the image space. This results in artifacts.

On the other hand, the z-direction filter convolution method to be applied to an image space has the advantage that since a tomographic image expressing a large slice thickness is produced by convoluting a z-direction filter to the image space, z-direction filtering is achieved accurately and the tomographic image enjoys high image quality. The disadvantage of the z-direction filter convolution method to be applied to the image space is that a processing time is long because a plurality of tomographic images are reconstructed in the z direction.

As mentioned above, the two techniques for controlling a slice thickness each have an advantage and a disadvantage. As long as the multi-array X-ray detector 24 is a small multi-array X-ray detector including sixteen detector arrays and having an X-ray detector width in the z direction of about 20 mm, the z-direction filter convolution method to be applied to projection data items has been generally adopted in the past. This is because it has taken much time for image back projection in the past. Therefore, the projection data space z-direction filter convolution in which image back projection is repeated a small number of times has been preferred to the image space z-direction filter convolution in which image back projection is repeated many times.

In the projection data space z-direction filter convolution, a weight coefficient filter is convoluted to projection data items in the z direction that is the direction of arrays. Thereafter, reconstruction function convolution and image back projection are each performed once. An image reconstruction time is therefore short.

However, since the width in the z direction of the multi-array X-ray detector 24 has increased, the z-direction filter convolution to be applied to projection data items may cause inconsistency. For example, assuming that a width of projection data items to which the z-direction filter is applicable is equivalent to, as shown in FIG. 9, four arrays, projection data items to which the z-direction filter applicable to the width equivalent to four arrays is convoluted irrespective of the positions of pixels in a tomographic image are three-dimensionally back-projected.

Figure 9:
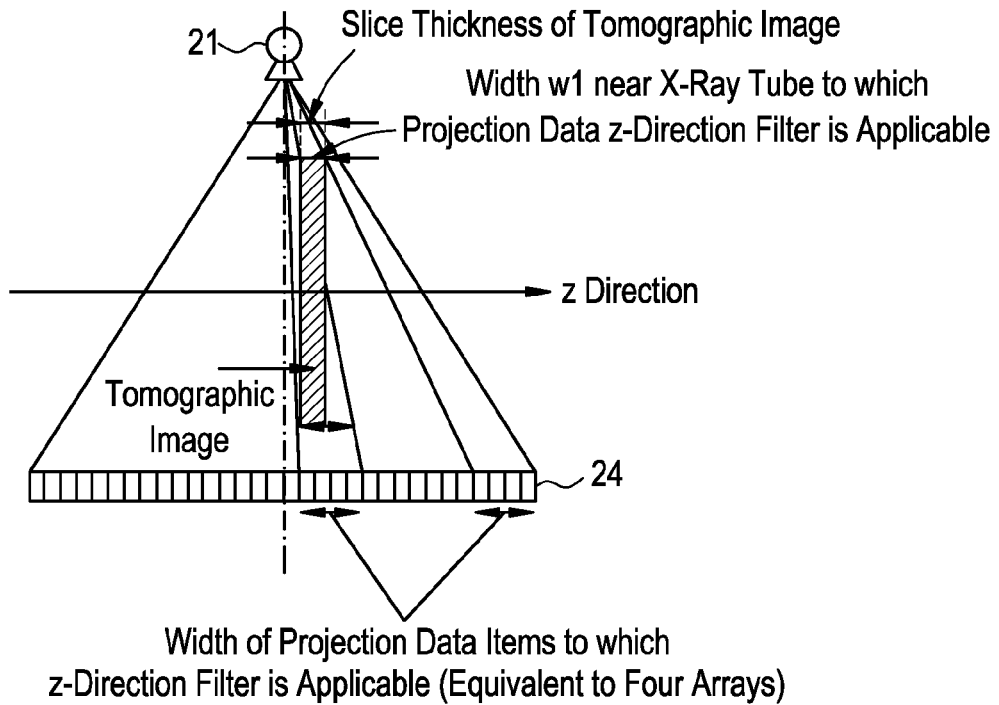
FIG. 9 shows inconsistency in a width to which a projection data z-direction filter is applicable.

As shown in FIG. 9, a width of pixels in a tomographic image that are presumed to lie near the X-ray tube 21 to which the projection data z-direction filter is applicable is w1. Moreover, a width of pixels in the tomographic image that are presumed to lie near the multi-array X-ray detector 24 to which the projection data z-direction filter is applicable is w2. In this case, the relationship of w2>w1 is apparently established.

As a slice thickness expressed by a tomographic image to be reconstructed gets larger, the above phenomenon becomes more obvious. Moreover, when the width of an X-ray beam to be back-projected varies, as indicated by the relationship of w2>w1, depending on a position in a tomographic image, artifacts occurs in the tomographic image. Namely, as a slice thickness expressed by a tomographic image to be reconstructed gets larger, the projection data z-direction filter convolution is likely to cause artifacts.

In helical scanning, as a helical pitch is smaller, z-direction positions expressed by data items extending over the width w1 corresponding to the width of an X-ray beam are different from those expressed by data items extending over the width w2 corresponding to the width of the X-ray beam. Consequently, artifacts are likely to occur.

In contrast, as far as the image space z-direction filter convolution is concerned, tomographic images 1, 2, and 3 expressing a small slice thickness are, as shown in FIG. 10, produced in advance. In the tomographic images expressing a small slice thickness, inconsistency in positions of pixels in a tomographic image caused by a difference in the width of an X-ray beam is minor. Artifacts hardly occur but image quality is high. Since the image space z-direction filter convolution is performed on the high-quality images expressing the small slice thickness, a finally reconstructed tomographic image of a large slice thickness still enjoys high image quality.

As apparent from the above description, the projection data space z-direction filter convolution is suitable for reconstruction of an image expressing a small slice thickness, while the image space z-direction filter convolution is suitable for reconstruction of an image expressing a large slice thickness.

When an image of a large slice thickness is reconstructed, an image reconstruction time is shortened by performing the projection data space z-direction filter convolution so as to express a slice thickness that is too small to cause artifacts stemming from inconsistency caused by a difference in an X-ray beam width. For a larger slice thickness, the image space z-direction filter convolution should be adopted.

Referring to the flowchart of FIG. 3, when the projection data space z-direction filter convolution of step S4 is performed, the projection data space z-direction filter is convoluted in order to express a slice thickness that is too small to cause artifacts stemming from inconsistency caused by a difference in an X-ray beam width. When a slice thickness need to be increased, the image space z-direction filter convolution of step S7 is performed in order to express a final slice thickness.

Figure 16:
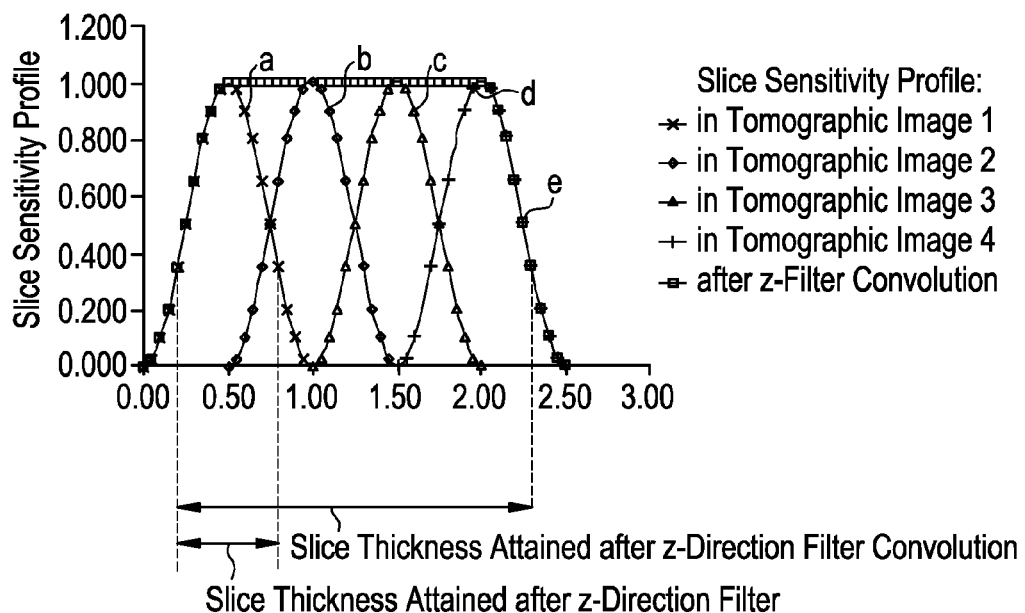
FIG. 16 shows slice sensitivity profiles concerning image space z-direction filter convolution.

FIG. 16 shows slice thicknesses indicated by slice sensitivity profiles expressed by tomographic images that have not undergone image space z-direction filter convolution that is performed as z-direction filter convolution, and slice thicknesses indicated by slice sensitivity profiles expressed by tomographic images having undergone the image space z-direction filter convolution. As apparent from the drawing, the slice thickness is controlled by the image space z-direction filter convolution.

The balance between the projection data space z-direction filter convolution and the image space z-direction filter convolution depends on a slice thickness and the width in the direction of arrays of each of X-ray detector channels included in the multi-array X-ray detector 24. Moreover, as far as helical scanning is concerned, the balance also depends on a helical pitch. Therefore, after the slice thickness, the width in the direction of arrays of the X-ray detector, and the helical pitch are determined, projection data space z-direction filter coefficients and image space z-direction filter coefficients should be optimized.

Figure 11:
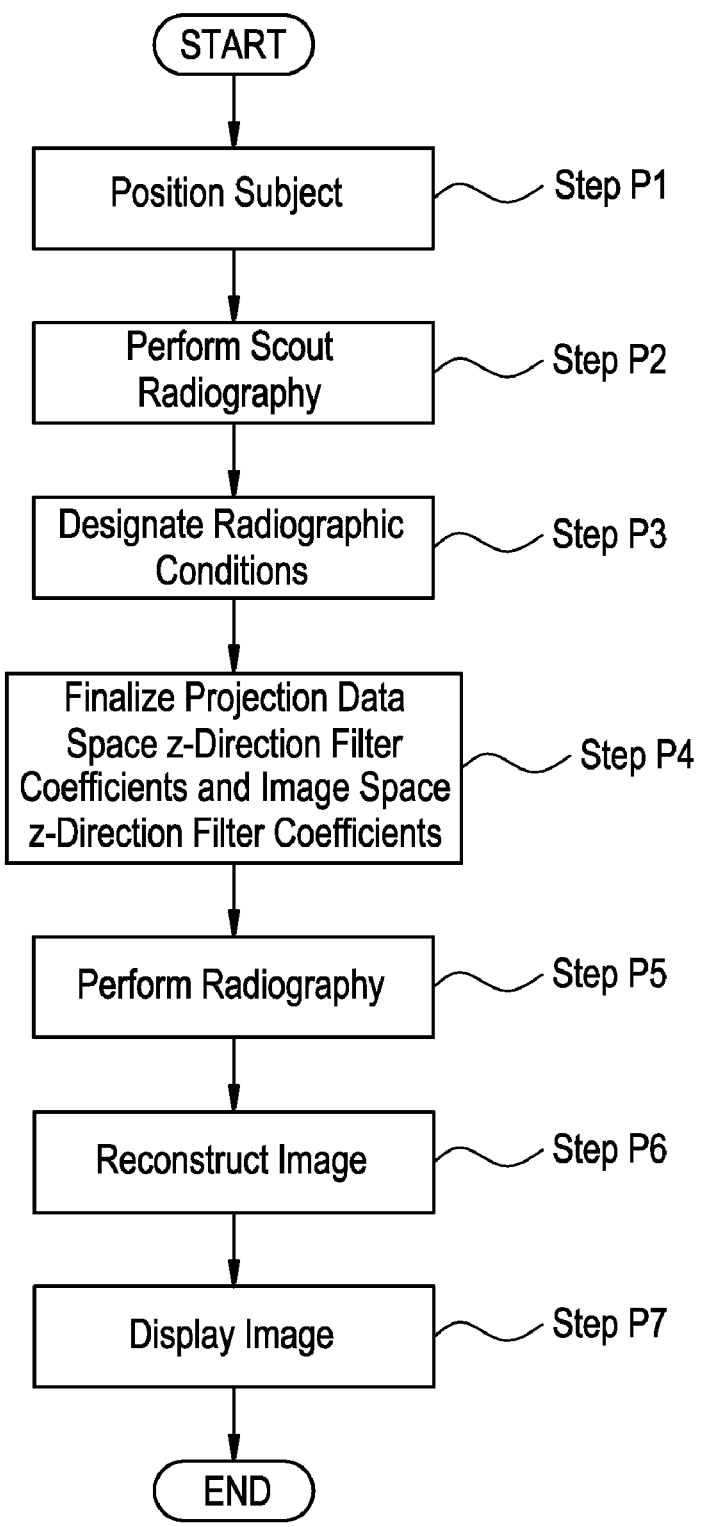
FIG. 11 is a flowchart describing a radiographic flow.

FIG. 11 describes a radiographic flow.

At step P1, a subject is positioned. At this time, the direction of the subject's body axis is regarded as the z direction, and a plane to be expressed by a tomographic image and to be radiographed and the rotational plane of the scanner gantry 20 are regarded as the xy plane.

At step P2, scout radiography is performed.

At step P3, radiographic conditions are designated. A scout image is produced in an AP direction (0° in the y direction), an LR direction (90° in the x direction), or both of the directions. An operator designates a position of radiography, a range of radiography, a spacing between tomographic images, a slice thickness of each tomographic image, the number of tomographic images, the width in the z direction of an X-ray detector employed, the number of arrays, and the width of each array. For a helical scan, the operator also designates a helical pitch. For a cine scan, the operator also designates the number of data acquisitions or a data acquisition time. Moreover, the operator may also designate as an image quality-related parameter a noise index value that is a target value concerning image noise (standard deviation of a pixel value), or an artifact index value that is a target value concerning the magnitude of artifacts in an image.

At step P4, projection data space z-direction filter coefficients and image space z-direction filter coefficients are adjusted dependently on the slice thickness, the number of X-ray detector arrays, the width of each array, and the helical pitch for a helical scan or a variable-pitch helical scan which are designated at step P3. The projection data space z-direction filter coefficients and image space z-direction filter coefficients are then finalized.

At step P5, a conventional (axial) scan, a cine scan, a helical scan, or a variable-pitch helical scan is performed based on the radiographic conditions designated at step P3.

At step P6, the projection data space z-direction filter coefficients designated at step P4 are used to perform projection data space z-direction filter convolution so as to express a certain slice thickness. Furthermore, the image space z-direction filter coefficients are used to perform image space z-direction filter convolution so as to express a final slice thickness. Thus, the slice thickness is controlled in order to reconstruct an image.

At step P7, the resultant image is displayed. If necessary, three-dimensional image display or multi-planar reformation (MPR) image display is performed.

Consequently, a tomographic image of optimal quality is reconstructed based on the slice thickness, the width in the direction of arrays of the X-ray detector, and the helical pitch designated as the respective radiographic conditions.

Figure 12:
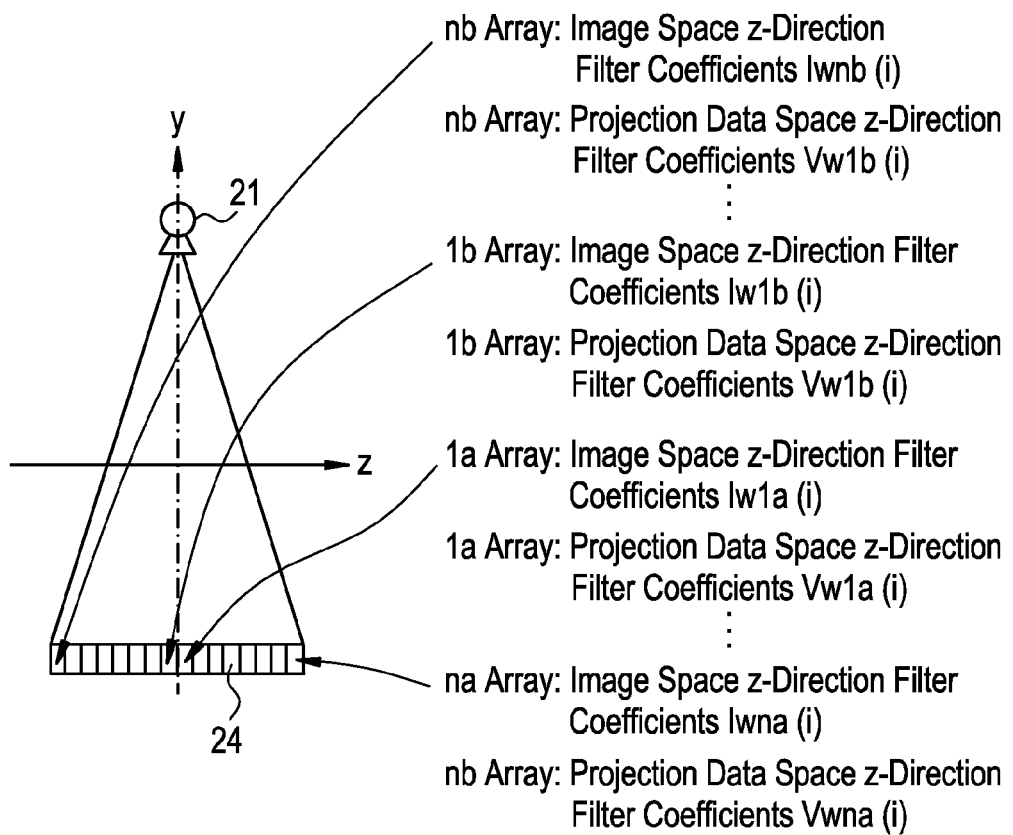
FIG. 12 shows image space z-direction filter coefficients dependent on the position of an X-ray detector array.
Figure 13A:
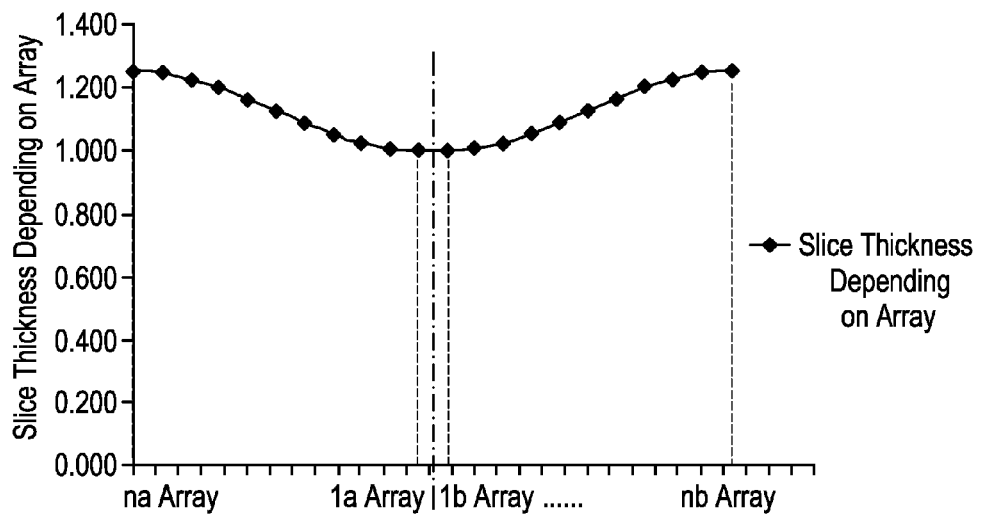
FIG. 13(a) shows a variation of a slice thickness dependent on each array.
Figure 13B:
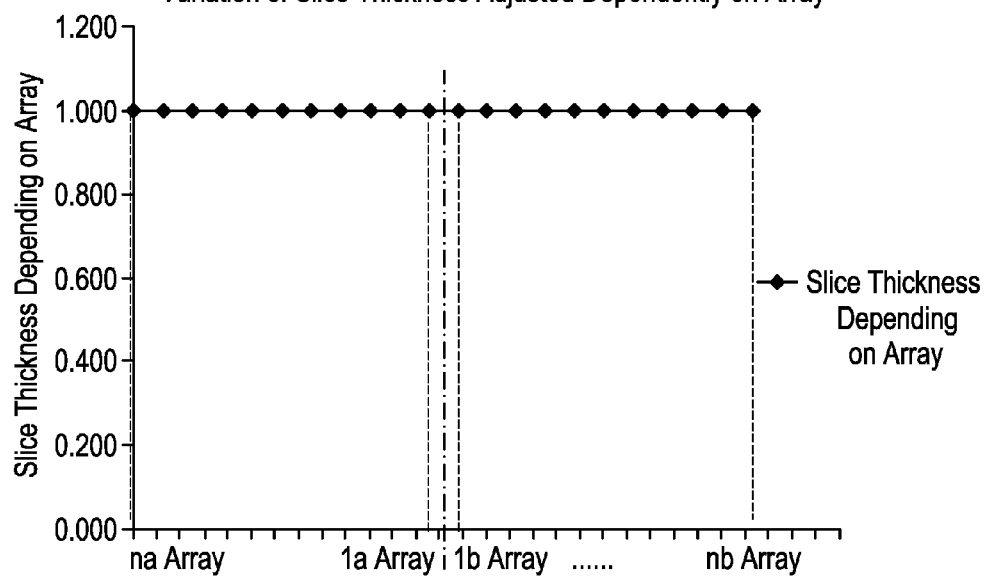
FIG. 13(b) shows a variation of a slice thickness adjusted dependently on each array.

Especially when a conventional (axial) scan or a cine scan is performed, if the detector arrays are numbered as shown in FIG. 12, a slice thickness may, as shown in FIG. 13(*a*) and FIG. 13(*b*), vary depending on an array in case image reconstruction is performed without position data space z-direction filter convolution or image space z-direction filter convolution. This is attributable to various factors including a crosstalk caused by the X-ray detector or adjustment of a three-dimensional image reconstruction algorithm. In this case, when three-dimensional image display or MPR image display is performed at step S7, an image displayed may become inhomogeneous in the z direction. In order to avoid this event, the projection data space z-direction filter coefficients for the projection data space z-direction filter convolution or the image space z-direction filter coefficients for the image space z-direction filter convolution are associated with each array and adjusted depending on an array. Consequently, the slice thickness becomes, as shown in FIG. 13(*b*), nearly uniform over the arrays.

Figure 14A:
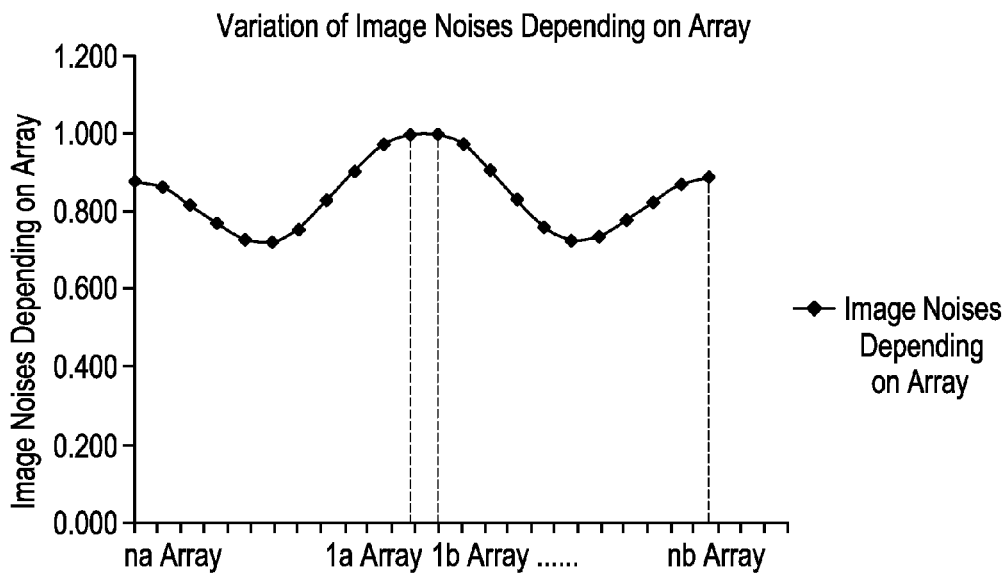
FIG. 14(a) shows a variation of image noises dependent on each array.
Figure 14B:
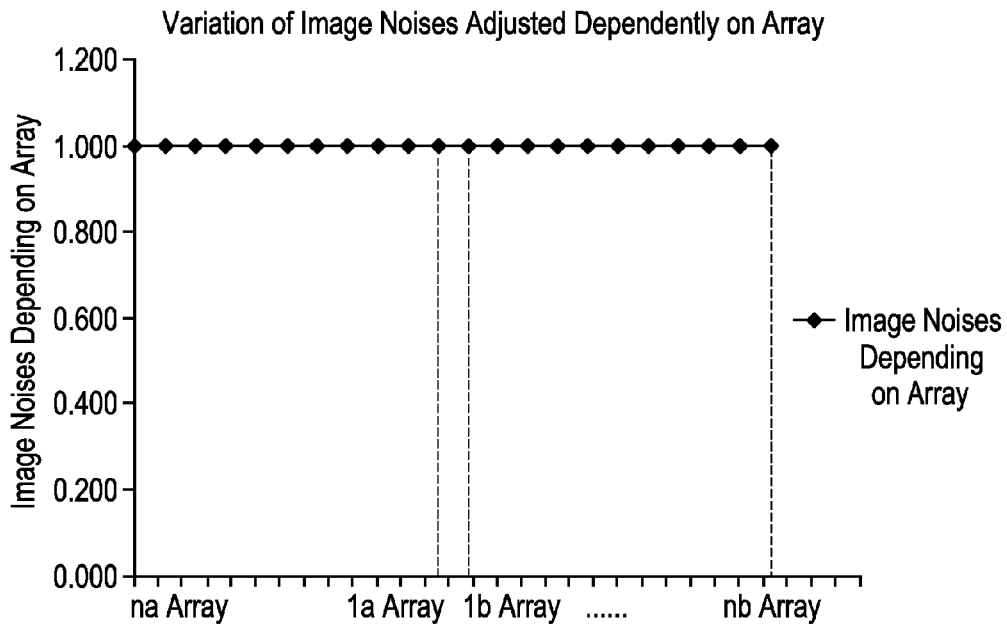
FIG. 14(b) shows a variation of image noises adjusted dependently on each array.

Image noises may vary depending on an array. For example, as shown in FIG. 14(*a*) and FIG. 14(*b*), image noises may depend on an array. This is attributable to various factors including a crosstalk caused by the X-ray detector and adjustment of a three-dimensional image reconstruction algorithm. In this case, when three-dimensional image display or MPR image display is performed at step S7, an image displayed may become inhomogeneous in the z direction. In order to avoid this event, an image noise filter is applied so that the projection data space z-direction filter coefficients for projection data space z-direction filter convolution or the image space z-direction filter coefficients for image space z-direction filter convolution will be associated with each array and adjusted depending on an array. Consequently, the image noises becomes, as shown in FIG. 14(*b*), nearly uniform over the arrays.

As mentioned above, in order to keep various image properties uniform, the projection data space z-direction filter coefficients for projection data space z-direction filter convolution or the image space z-direction filter coefficients for image space z-direction filter convolution are associated with each array and adjusted dependently on an array.

Specifically, as shown in FIG. 12, image space z-direction filter coefficients IZnb(i) and projection data space z-direction filter coefficients VZnb(i) are associated with an nb array. Image space z-direction filter coefficients IZ1b(i) and projection data space z-direction filter coefficients VZ1b(i) are associated with an 1b array. Image space z-direction filter coefficients IZ1a(i) and projection data space z-direction filter coefficients VZ1a(i) are associated with an 1a array. Image space z-direction filter coefficients IZna(i) and projection data space z-direction filter coefficients VZna(i) are associated with an na array. Thus, filter coefficients are associated with each array.

Herein, when i denotes 5, z-direction (direction-of-arrays) filter coefficients are associated with five respective arrays and expressed by the formula (12) below.

$$[Iwnb(1), Iwnb(2), Iwnb(3), Iwnb(4), Iwnb(5)] \quad (12)$$

Figure 15:
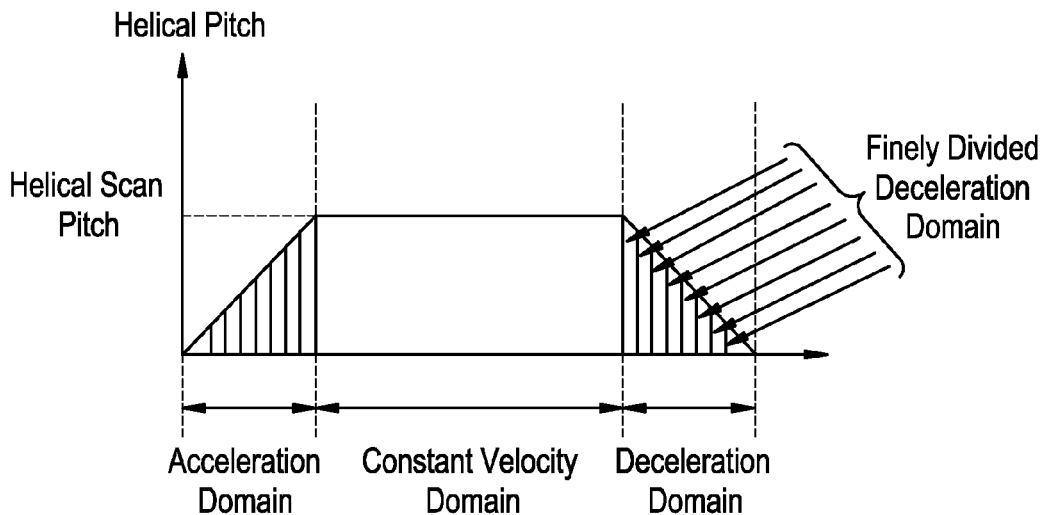
FIG. 15 shows a change of helical pitches for a variable-pitch helical scan.

Moreover, a helical pitch especially for a variable-pitch helical scan changes from one to another as shown in FIG. 15.

Relative to a constant velocity domain in the drawing, coefficient parameters including the image space z-direction filter coefficients IZnb(i) and projection data space z-direction coefficients VZnb(i) associated with the nb array, the image space z-direction filter coefficients IZ1b(i) and projection data space z-direction coefficients VZ1b(i) associated with the 1b array, the image space z-direction filter coefficients IZ1a(i) and projection data space z-direction coefficients VZ1a(i) associated with the 1a array, and the image space z-direction filter coefficients IZna(i) and projection data space z-direction coefficients VZna(i) associated with the na array may be fixed to one set of values. Relative to an acceleration or deceleration domain in the drawing, the change of helical pitches cannot be handled using one set of coefficient parameters. As shown in FIG. 15, the acceleration or deceleration domain is finely divided into sub domains. The coefficient parameters may be varied depending on velocities falling within each sub domain, or the coefficient parameters may be associated with a parameter of a z-coordinate or a time instant t as a function of each z-coordinate or each time instant.

The influence of the processing times required for the projection data space z-direction filter convolution and image space z-direction filter convolution respectively on an image reconstruction time will be described below.

Figure 17:
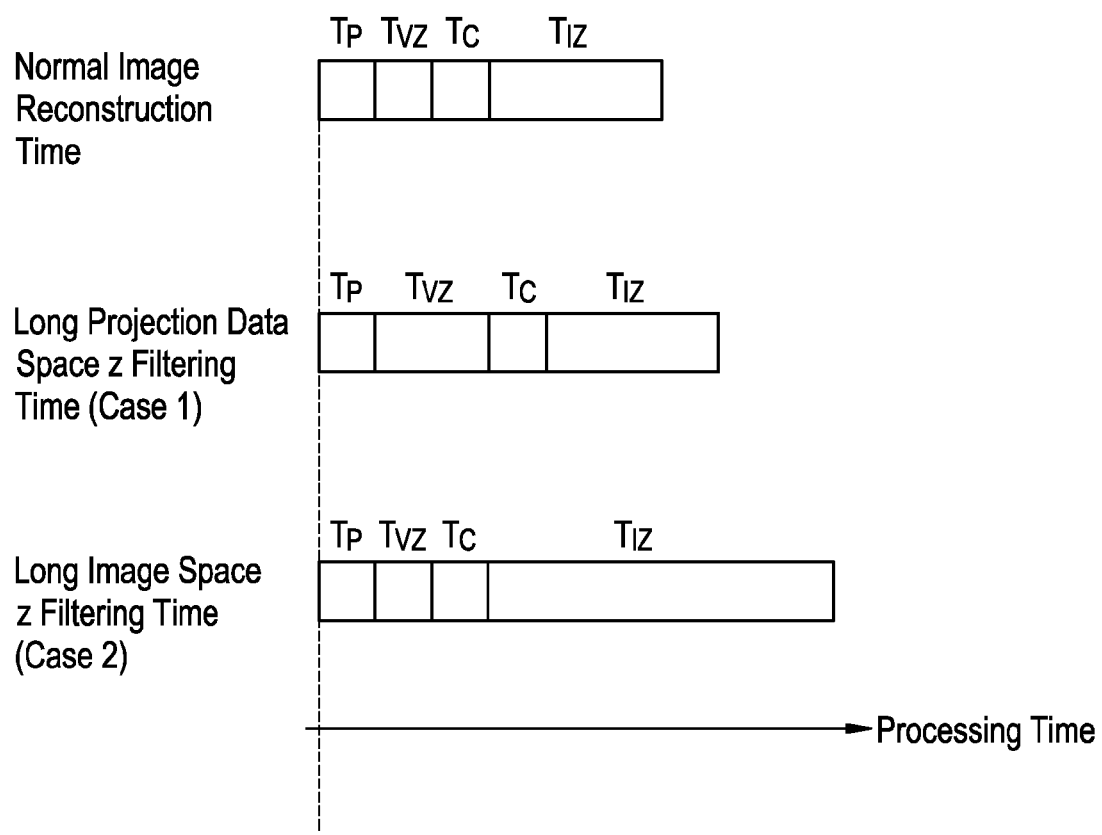
FIG. 17 shows influence of projection data space z filer convolution and image space z filter convolution on an image reconstruction time.

In FIG. 17, a time base is set on the axis of abscissas, and examples of processing times required in different cases are juxtaposed on the axis of ordinates.

As shown in FIG. 17, an image reconstruction time is usually composed of a preprocessing time $T_P$ (including steps S1, S2, and S3 in FIG. 3), a projection data space z-direction filter convolution time $T_{vz}$ (including step S4 in FIG. 3), a reconstruction function convolution time $T_C$ (including step S5 in FIG. 3), and an image space z-direction filter convolution time $T_{IZ}$ (including steps S6, S7, and S8 in FIG. 3).

In this case, $T_{IZ}$ shall be nearly equal to $3 \cdot T_{VZ}$. If emphasis is put on the z filtering in the projection data space, Case 1 in the drawing holds true. If emphasis is put on the z filtering in the image space, Case 2 in the drawing holds true.

As seen from the above description, the image space z filtering requires a long processing time. However, the image space z filtering ensures high image quality. The processing time and image quality are trade-offs. When the image space z filtering is combined with the projection data z filtering that does not require a long processing time but brings about deteriorated image quality, optimization is needed in terms of the image quality and processing time.

Figure 18:
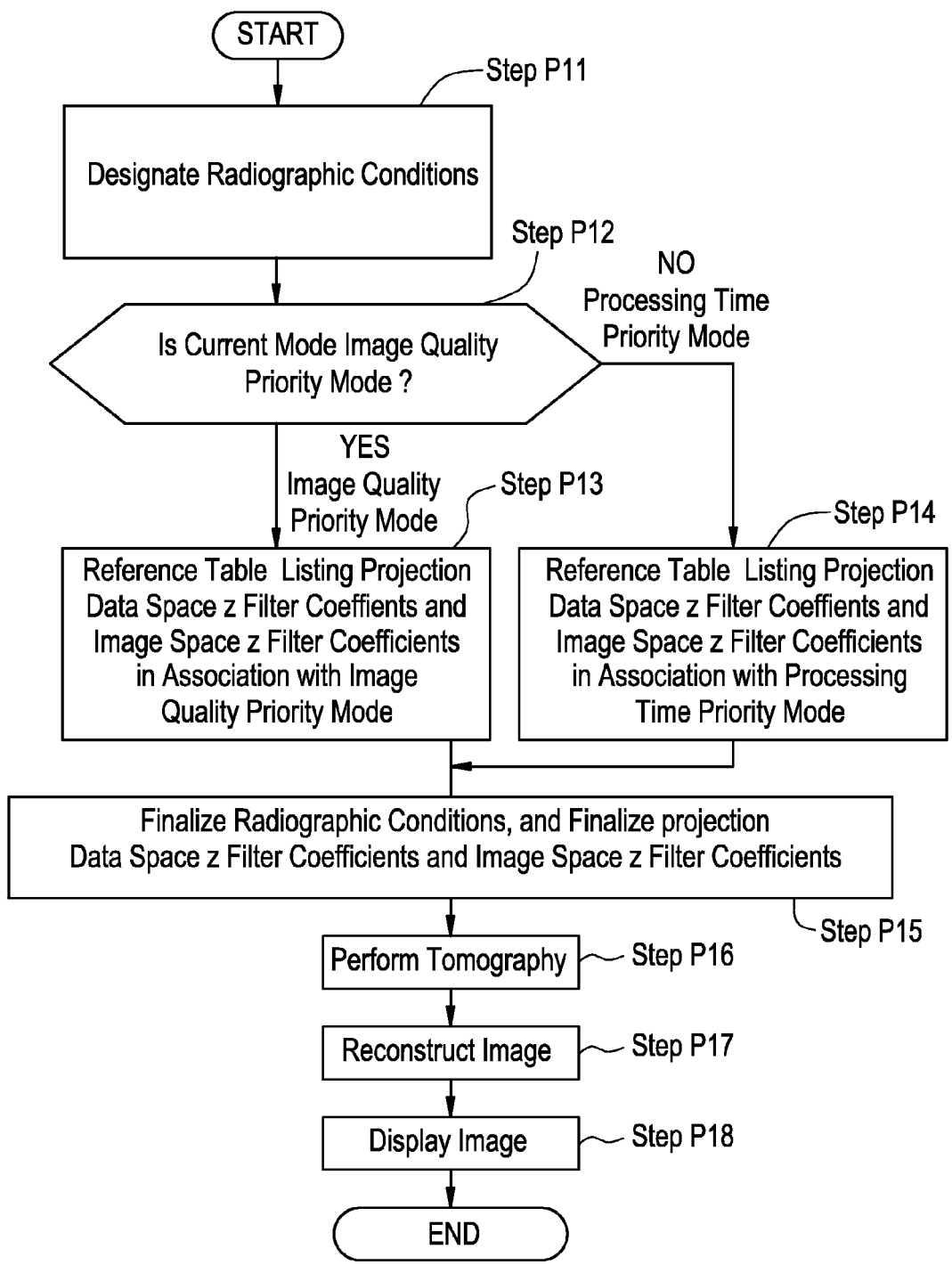
FIG. 18 is a flowchart describing tomography supporting an image quality priority mode and a processing time priority mode.

In the present embodiment, an image quality priority mode and a processing time priority mode are switched for tomography as described below. In a selected mode, the projection data space z filter coefficients and image space z filter coefficients are optimized and tomography is performed as shown in FIG. 18.

At step P11, radiographic conditions are designated. At this time, an operator may select either of the image quality priority mode and processing time priority mode. Otherwise, either of the modes may be designated as one of the radiographic conditions recommended for each region.

At step P12, a current mode is checked to see if it is the image quality priority mode. If the image quality priority mode is selected as an affirmative reply, control is passed to step P13. If the processing time mode is selected as a negative reply, control is passed to step P14.

At step P13, a table listing the projection data space z filter coefficients and image space z filter coefficients in association with the image quality priority mode is referenced.

At step P14, a table listing the projection data space z filter coefficients and image space z filter coefficients in association with the processing time priority mode is referenced.

At step P15, the radiographic conditions are finalized and the projection data space z filter coefficients and image space z filter coefficients are finalized.

At step P16, tomography is performed.

At step P17, an image is reconstructed.

At step P18, an image is displayed.

As for the table listing the projection data space z filter coefficients and image space z filter coefficients in association with each set of radiographic conditions which is referenced at step P13 or P14, an example employed in helical scanning is shown in FIG. 19. The table is provided for each region, each object to be examined, each multi-array X-ray detector mode, each radiography mode, and each priority mode. In the example employed in helical scanning and shown in FIG. 19, the projection data space z filter coefficients ITZhxx and image space z filer coefficients VZhxx are determined in association with each helical pitch. Herein, xx denotes a number assigned to coefficients.

As mentioned above, the projection data space z-direction filter coefficients and image space z-direction filter coefficients are controlled relative to each set of radiographic conditions, whereby image quality is optimized.

For example, in the image quality priority mode, the projection data space z-direction filter coefficients and image space z-direction filter coefficients are controlled in relation to each helical pitch and each index value indicating each image quality-related property, for example, artifacts or image noises. Thus, image quality can be optimized.

The projection data space z filter coefficients IZxx and image space z filter coefficients VZxx are adjusted in advance using a tomographic image of a phantom or a standard subject, whereby image quality can be held optimal.

Figure 21A:
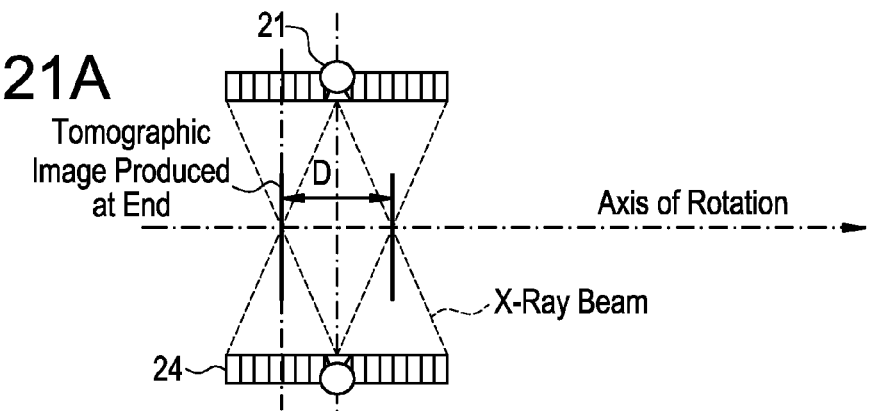
FIGS. 21a, 21b, and 21c show an overlap pitch occurring in a case where a plurality of positions in a z direction are scanned.
Figure 21B:
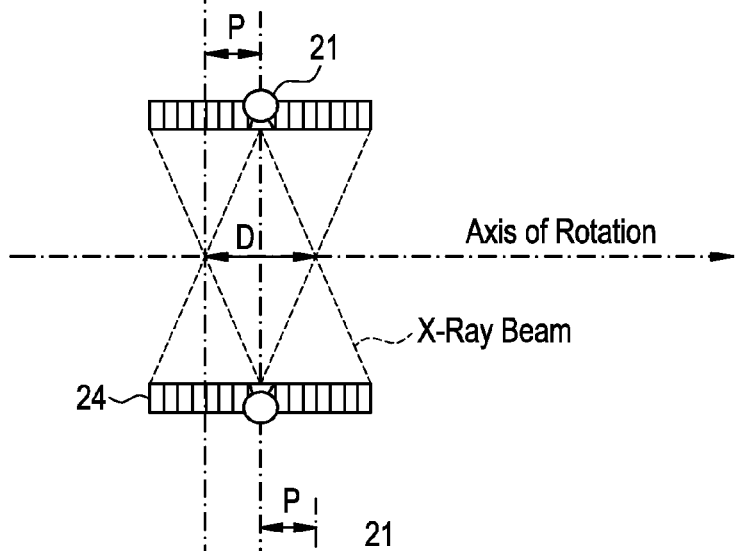
Figure 21C:
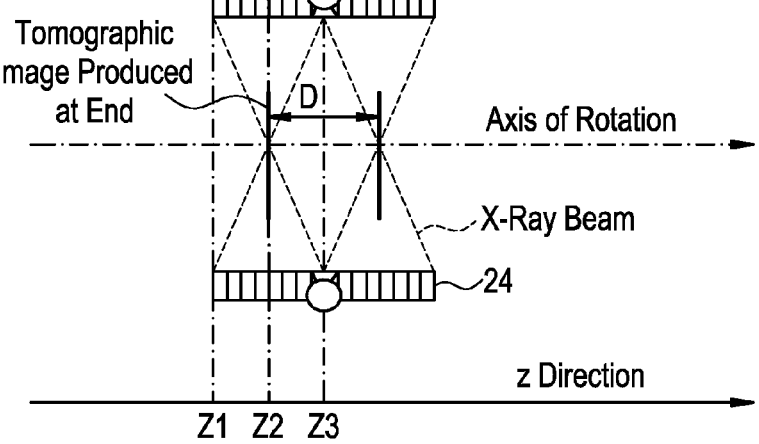

FIG. 20 shows a table listing the projection data space z filter coefficients and image space z filter coefficients in association with each set of photographic conditions for a conventional (axial) scan. In the case of three-dimensional image reconstruction, whichever of a conventional (axial) scan and a cine scan is performed, projection data space z filtering may be performed. Moreover, image space z filtering may also be performed. Similarly to the case of a helical scan, the projection data space z filter coefficients VZaxx and image space z filter coefficients IZaxx can be optimized according to radiographic conditions. In the example shown in FIG. 20, the projection data space z filter coefficients and image space z filter coefficients are controlled relative to each image quality-related property, for example, an artifact index value according to an overlap pitch shown in FIG. 21. Thus, image quality is optimized. Herein, the overlap pitch is, as shown in FIG. 21(a), FIG. 21(b), and FIG. 21(c), a ratio of a distance P, by which the X-ray tube 21 and multi-array X-ray detector 24 are moved in the z direction during a conventional (axial) scan, to the width D in the z-axis direction of the multi-array X-ray detector 24 in the center of rotation. Namely, P/D is the overlap pitch.

Moreover, similarly to the case where a helical scan is performed, the projection data space z filter coefficients IZxx and image space z filter coefficients VZxx are adjusted in advance using a tomographic image of a phantom or a standard subject. Thus, image quality can be held optimal.

Even when a cine scan is performed, the table listing projection data space z filter coefficients and image space z filter coefficients in association with each set of radiographic conditions, which is shown in FIG. 20, may be defined. In the case where a conventional (axial) scan is performed, similarly to the case where a cine scan is performed, artifacts in a tomographic image caused by X-ray detector arrays located at the ends of the X-ray detector in the z direction pose a problem. Therefore, the table listing the projection data space z filter coefficients and image space z filter coefficients in association with each set of radiographic conditions is important.

FIG. 22 shows a table listing projection data space z filter coefficients and image space z filter coefficients in association with each set of radiographic conditions for a variable-pitch helical scan. When three-dimensional image reconstruction is employed, even if the variable-pitch helical scan is performed, as long as an X-ray tube current is controlled in the z direction, a tomographic image whose image quality is uniform over the z direction can be produced. Namely, a tomographic image whose image quality-related properties, such as, artifacts, a slice thickness, and noises are nearly uniform over the z direction can be produced. In this case, optimization of the projection data space z filter and image quality z filter in relation to each of helical pitches to be changed has a significant meaning.

In the example shown in FIG. 22, the projection data space z filter coefficients and image space z filter coefficients are optimized in order to optimize image quality-related properties including noises and artifacts in relation to a maximum helical pitch set for a variable-pitch helical scan or a shuttle-mode variable-pitch helical scan. In this case, the filter coefficients are determined in association with the maximum helical pitch. Since the helical pitch changes from 0 to a maximum value, the projection data space z filter coefficients and image space z filter coefficients are optimized relative to each helical pitch. Otherwise, the projection data space z filter coefficients and image space z filter coefficients may be determined as functions of each parameter that is each helical pitch.

Figure 23:
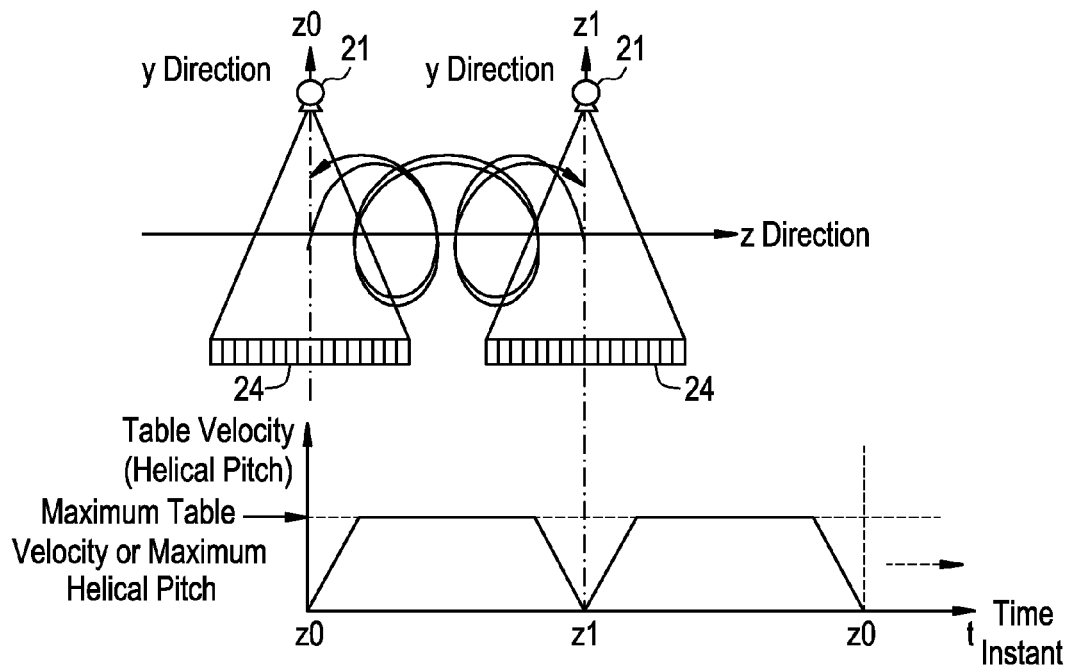
FIG. 23 shows movements made in a shuttle-mode variable-pitch helical scan.

The shuttle-mode variable-pitch helical scan, shown in FIG. 23, is a scan mode in which a variable-pitch helical scan is repeatedly performed a plurality of times within a range defined with z-coordinates [z0, z1] with the table accelerated or decelerated. The shuttle-mode variable-pitch helical scan is employed in perfusion or any other examination.

Figure 24:
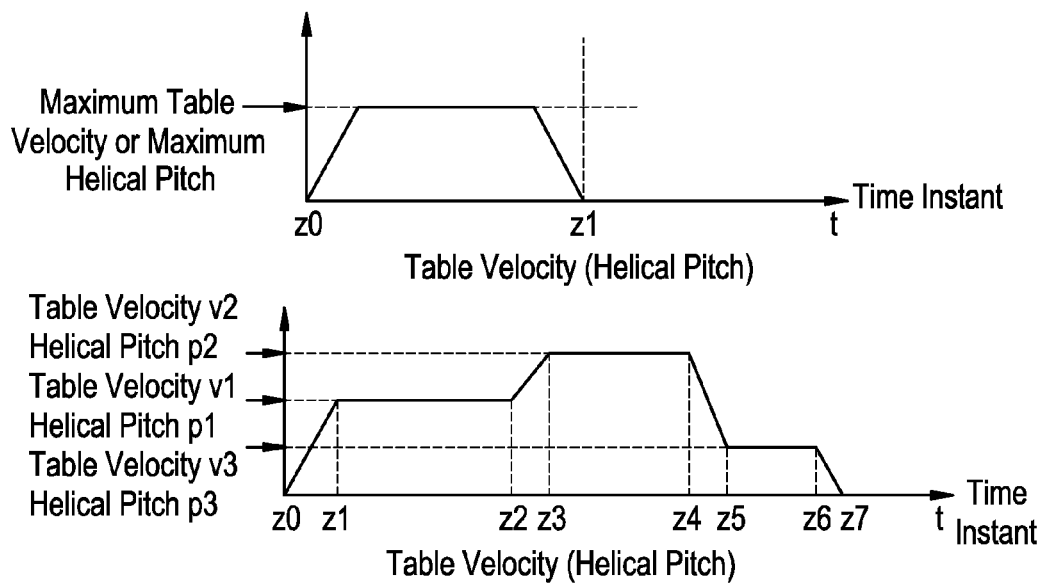
FIG. 24 shows movements made in a variable-pitch helical scan.

In contrast, the normal variable-pitch helical scan, shown in FIG. 24, is a scan mode in which a range defined with z-coordinates [z0, z1] is scanned by varying a helical pitch and accelerating or decelerating the table.

In an evolved mode, a range defined with z-coordinates [z0, z7] is scanned at a table velocity v1 and a helical pitch p1. Another z-coordinate range [z1, z2] is scanned at a table velocity v2 and a helical pitch p2. Another z-coordinate range [z3, z4] is scanned at a table velocity v3 and a helical pitch p3. Another z-coordinate coordinate range [z5, z6] is helically scanned at a constant velocity. A variable-pitch helical scan is performed on another z-coordinate range [z0, z1] by accelerating the table. A variable-pitch helical scan is performed on another z-coordinate range [z2, z3] by accelerating the table. A variable-pitch helical scan is performed on another z-coordinate range [z4, z5] by decelerating the table. A variable-pitch helical scan is performed on another z-coordinate range [z6, z7] by decelerating the table. This mode would prove effective in a case a plurality of organs or a plurality of regions to be examined are helically and quickly scanned.

As mentioned above, in the X-ray CT apparatus 100 of the present embodiment, the scanner gantry 20 performs a scan to irradiate X-rays to a subject while rotating about the subject, and to detect X-rays transmitted by the subject, and obtains projection data items. Herein, the scanner gantry 20 includes the X-ray tube 21 that rotates about a subject and irradiates X-rays to the subject, and the multi-array X-ray detector 24 that detects X-rays having been irradiated from the X-ray tube 21 and transmitted by the subject. The X-ray tube 21 irradiates conical X-rays that fan out in the direction of channels extending in a direction of rotation in which the X-ray tube is rotated with a subject as a center, and the direction of arrays z extending in the direction of an axis of rotation. The multi-array X-ray detector 24 has a plurality of X-ray detector elements, which detect X-rays having been irradiated from the X-ray tube 21 and transmitted by the subject, arrayed in the form of a matrix in the direction of channels and the direction of arrays. In the X-ray CT apparatus 100, the central processing device 3 reconstructs a subject's slice image on the basis of projection data items which the scanner gantry 20 produces by performing a scan. Herein, the central processing device 3 performs first Z filtering (projection data space z-direction filtering) on the projection data items, which are produced by performing a scan, in the direction of arrays z. Based on the projection data items having undergone the first Z filtering, a plurality of first slice images expressing a first slice thickness are produced as if to be juxtaposed in the direction z of arrays. Thereafter, second Z filtering (image space z-direction filtering) is performed on the first slice images in the direction Z of arrays in order to produce a second slice image expressing a second slice thickness larger than the first slice thickness. Namely, the central processing device 3 performs projection data space z-direction filtering on projection data items that are produced by performing a scan in the direction z of arrays. Thereafter, a reconstruction function is convoluted to the projection data items having undergone the projection data z-direction filtering, and the resultant projection data items are three-dimensional back-projected in order to reconstruct a plurality of first slice images, which express a small slice thickness, as if the first slice images were juxtaposed in the direction of arrays. Image space z-direction filtering is performed in order to convolute a direction-of-arrays (z-direction) filter to the plurality of first slice images expressing a small slice thickness, whereby a second slice image expressing a large slice thickness is reconstructed. For image reconstruction, the central processing device adjusts filter coefficients employed in the first Z filtering and filter coefficients employed in the second Z filtering according to radiographic conditions, and differentiates the slice thicknesses expressed by the first and second slice images. Consequently, the X-ray CT apparatus 100 in accordance with the present embodiment can improve image quality and speed up reconstruction computing.

Specifically, according to the X-ray CT apparatus 100, when an X-ray CT apparatus including a two-dimensional area X-ray detector that is represented by a multi-array X-ray detector or a flat-panel X-ray detector and that has a matrix structure performs a conventional (axial) scan, a cine scan, or a helical scan, a slice thickness can be controlled and an image reconstruction time and image quality can be optimized.

Incidentally, the implementation of the present invention is not limited to the aforesaid embodiment, but various variants can be adopted.

For example, an image reconstruction method may be a three-dimensional image reconstruction method based on a known Feldkamp technique or any other three-dimensional image reconstruction method.

In the present embodiment, a direction-of-array (z-direction) filter having different coefficients associated with respective arrays is convoluted in order to adjust a variance of image quality and realize a uniform slice thickness and uniform image quality in terms of artifacts and noises over the arrays. Various filter coefficients are conceivable and expected to provide the same advantage.

Although the present embodiment has been described on the assumption of an X-ray CT apparatus for medical use, it can be adapted to an X-ray CT apparatus for industrial use or an X-ray CT-PET apparatus or X-ray CT-SPECT apparatus that is realized by combining an X-ray CT apparatus with other modality. As for the present embodiment, FIG. 17 presents processing times required in respective cases. The processing times vary depending on an image reconstruction means. Maximization of projection data space z filter coefficients and image space z filter coefficients therefore varies depending on the image reconstruction means. The processing times can be optimized based on the same idea as the described one.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray CT apparatus comprising:
   an X-ray data acquisition device for acquiring projection data items of X-rays transmitted by a subject positioned between an X-ray generator and a two-dimensional X-ray area detector that is opposed to the X-ray generator, that detects X-rays, that is represented by a multi-array X-ray detector or a flat-panel X-ray detector, and that has a matrix structure, while rotating the X-ray generator and two-dimensional X-ray area detector about a center of rotation located between the X-ray generator and two-dimensional X-ray area detector;
   an image reconstruction device for reconstructing an image using projection data items acquired by the X-ray data acquisition device;
   an image display device for displaying a reconstructed tomographic image; and
   a radiographic condition designation device for designating radiographic conditions for tomography, wherein:
   the image reconstruction device controls a slice thickness by employing z-direction filter convolution in an image space after employing z-direction filter convolution in a projection data space.

2. The X-ray CT apparatus according to claim 1, wherein the image reconstruction device changes at least one of projection data space z-direction filter coefficients and image space z-direction filter coefficients according to each set of radiographic conditions for tomography designated by the radiographic condition designation device.

3. The X-ray CT apparatus according to claim 1, wherein the image reconstruction device changes at least one of projection data space z-direction filter coefficients and image space z-direction filter coefficients according to an image quality-related radiographic condition for tomography designated by the radiographic condition designation device.

4. The X-ray CT apparatus according to claim 1, having:
   the radiographic condition designation device that designates at least one of an image noise index and an artifact index; and
   the image reconstruction device that changes at least one of image space z-direction filter coefficients and projection data space z-direction filter coefficients according to at least one of the image noise index and artifact index.

5. The X-ray CT apparatus according to claim 1, having the image reconstruction device that changes at least one of projection data space z-direction filter coefficients and image space z-direction filter coefficients according to radiographic conditions for tomography relevant to a radiography time and radiographic efficiency designated by the radiographic condition designation device.

6. The X-ray CT apparatus according to claim 1, having the image reconstruction device that employs three-dimensional image reconstruction.

7. The X-ray CT apparatus according to claim 1, having the image reconstruction device that changes image space z-direction filter coefficients and projection data space z-direction filter coefficients dependently on a slice thickness of a tomographic image.

8. The X-ray CT apparatus according to claim 1, having the image reconstruction device that changes image space z-direction filter coefficients and projection data space z-direction filter coefficients dependently on the width of each array included in the X-ray detector in a direction of arrays and the number of arrays.

9. The X-ray CT apparatus according to claim 1, having the image reconstruction device that changes image space z-direction filter coefficients and projection data space z-direction filter coefficients dependently on the position of each pixel in a tomographic image of an xy plane reconstructed.

10. The X-ray CT apparatus according to claim 1, having the image reconstruction device that sets all image space z-direction filter coefficients to positive values.

11. The X-ray CT apparatus according to claim 1, having the image reconstruction device that sets part of image space z-direction filter coefficients to negative values.

12. The X-ray CT apparatus according to claim 1, having the image reconstruction device tat sets all projection data space z-direction filter coefficients to positive values.

13. The X-ray CT apparatus according to claim 1, having the image reconstruction device that sets part of projection data space z-direction filter coefficients to negative values.

14. The X-ray CT apparatus according to claim 1, having the image reconstruction device that concurrently performs at least two of z-direction filter convolution in a projection data space, back projection, and z-direction filter convolution in an image space.

15. The X-ray CT apparatus according to claim 1, having the image reconstruction device that controls a slice thickness by employing projection data space z-direction filter convolution and image space z-direction filter convolution, and reconstructs a tomographic image by performing a helical scan.

16. The X-ray CT apparatus according to claim 1, having the image reconstruction device that controls a slice thickness by employing projection data space z-direction filter convolution and image space z-direction filter convolution, and reconstructs a tomographic image by performing a variable-pitch helical scan.

17. The X-ray CT apparatus according to claim 1, having the image reconstruction device that changes image space z-direction filter coefficients and projection data space z-direction filter coefficients dependently on a helical pitch set for a helical scan or a variable-pitch helical scan.

18. The X-ray CT apparatus according to claim 1, having the image reconstruction device that controls a slice thickness by employing projection data space z-direction filter convolution and image space z-direction filter convolution, and reconstructs a tomographic image by performing a conventional (axial) scan or a cine scan.

* * * * *